United States Patent [19]
Green et al.

[11] 3,931,167
[45] Jan. 6, 1976

[54] PROCESS FOR THE MANUFACTURE OF 3-KETO-6-AZIDO-4,6-BIS-DEHYDRO-STEROIDS AND INTERMEDIATES USEFUL THEREIN

[75] Inventors: Michael J. Green, East Brunswick, N.J.; Satish C. Bisarya, Moradabad, India

[73] Assignee: Schering Corporation, Kenilworth, N.J.

[22] Filed: June 10, 1974

[21] Appl. No.: 477,938

Related U.S. Application Data

[63] Continuation of Ser. No. 373,056, June 25, 1973, abandoned.

[52] U.S. Cl............. 260/239.55 R; 260/239.55 R, 260/397.4; 260/397.45; 260/397.47; 260/999
[51] Int. Cl.$^2$.................. C07J 1/00; C07J 5/00
[58] Field of Search........... 260/239.55 R, 239.55 D, 260/397.4, 397.45, 397.47, 349; /Machine Searched Steroids

[56] References Cited
UNITED STATES PATENTS

| | | |
|---|---|---|
| 3,026,320 | 3/1962 | Djerassi et al.............. 260/239.55 |
| 3,665,017 | 5/1972 | Teutsch et al................ 260/349 |
| 3,707,484 | 12/1972 | Rausser et al................ 260/349 |

OTHER PUBLICATIONS

Kelsy et al. Steroids, 18:3 pp. 261–279 (1971).

*Primary Examiner*—Ethel G. Love
*Attorney, Agent, or Firm*—Mary S. King

[57] ABSTRACT

Pharmacologically valuable 3-keto-6-azido-4,6-bis-dehydro-steroids are prepared by treating a 3-keto-6β,7-diacyloxy-4-dehydro-steroid, preferably a 3-keto-6β,7β-diacyloxy-4-dehydrosteroid, wherein said acyloxy group is a good leaving group (e.g. hydrocarbonsulfonyloxy), with an azide salt in a nonreactive organic solvent. Novel intermediates for this process, i.e. novel 3-keto-6β,7β-dihydroxy-4-dehydro-steroids and 6β,7β-dihydrocarbonsulfonyloxy-esters thereof, are conveniently prepared by treating a 3-keto-4,6-bis-dehydro-steroid with osmium tetroxide followed by reductive cleavage of the 6β,7β-osmate ester thereby formed, isolating and thence esterifying the resulting 3-keto-6β,7β-dihydroxy-4-dehydro-steroid with a hydrocarbonsulfonyl halide in a tertiary amine.

32 Claims, No Drawings ic resonance spectroscopy.
PROCESS FOR THE MANUFACTURE OF 3-KETO-6-AZIDO-4,6-BIS-DEHYDRO-STEROIDS AND INTERMEDIATES USEFUL THEREIN This application is a continuation of U.S. Ser. No. 373,056 filed June 25, 1973, now abandoned.

FIELD OF INVENTION

This invention relates to a novel process for the preparation of pharmacologically active 3-keto-6-azido-4,6-bis-dehydro-steroids, and to novel 3-keto-6$\beta$,7$\beta$-dihydrocarbonsulfonyloxy-4-dehydro-steroids useful as intermediates therein.

DESCRIPTION OF PRIOR ART 3-keto-6-azido-4,6-bis-dehydro-steroids are known compounds having pharmacological activity and/or being useful as intermediates in preparing other valuable steroidal derivatives. Prior art methods for preparing these compounds are described in U.S. Pat. Nos. 3,665,017 and 3,707,484 and comprise treating a 3-keto-6$\beta$-azido-7$\alpha$-acyloxy-4-dehydro-steroid which is saturated at C-1 and C-2 with a tetraalkylammonium halide in an aprotic solvent or with a hydrochloric acid-acetic acid mixture in an inert solvent.

By these prior art methods, a 6-azido-1,4,6-tri-dehydro-steroid cannot be obtained directly, it being necessary to first prepare a 3-keto-6-azido-4,6-bis-dehydro-steroid and then introduce the 1-dehydro bond by treatment with 2,3-dichloro-5,6-dicyanobenzoquinone (DDQ) in the presence of a strong acid and water. Additionally, when preparing a 3-keto-6-azido-4,6-dehydro-steroid having a 9$\alpha$-halogeno-11$\beta$-hydroxy system by the prior art methods, in order to minimize competing side reactions, it is necessary to esterify the hydroxyl group at C-11 prior to preparing the 6$\beta$-oxido-7$\alpha$-acyloxy intermediate, thus necessitating a second additional step of removing the ester at C-11 after the desired 6-azido-4,6-bis-dehydro-steroid has been prepared.

Our novel process whereby a 3-keto-6$\beta$,7$\beta$-dihydrocarbonsulfonyloxy-4-dehydro-steroid upon treatment with an azide salt in a nonreactive, organic solvent is converted to a 3-keto-6-azido-4,6-bis-dehydro-steroid, advantageously can be carried out on intermediates having a 1-dehydro bond and/or having a 9$\alpha$-halogeno-11$\beta$-hydroxy system and there is obtained directly the corresponding 3-keto-6-azido-1,4,6-tri-dehydro-steroid and/or 3-keto-6-azido-9$\alpha$-halogeno-11$\beta$-hydroxy-4,6-bis-dehydro (or 1,4,6-tri-dehydro) steroid. By our process, therefore, 3-keto-6azido-1,4,6-tridehydro-steroids and 3-keto-6-azido-9$\alpha$-halogeno-11$\beta$-hydroxy-4,6-bis (and 1,4,6-tri)-dehydro-steroids are made directly, eliminating the costly and time-consuming steps of DDQ - dehydrogenation and/or 11$\beta$-acyloxylation and thence 11$\beta$-hydrolysis required by prior art methods.

Described in the art (J. A. Zderic, H. Carpio, and C. Djerassi, J.O.C. 24, 909 (1959)) are 6$\alpha$,7$\alpha$-dihydroxycortisone acetate, 6$\alpha$,7$\alpha$-dihydroxy-9$\alpha$-fluorohydrocortisone acetate and 6$\alpha$,7$\alpha$-dihydroxyprednisolone acetate and their preparation by osymlation in dioxane of the corresponding 6,7-unsubstituted-6-dehydro analog, assignment of the $\alpha$-configuration having been made on the basis that it is the more probable configuration.

By our invention, we have found that when a 3-keto-6,7-unsubstituted-4,6-bis-dehydro-steroid is treated with osmiumtetroxide in dioxane there is formed a mixture of the corresponding 3-keto-6$\alpha$,7$\alpha$-dihydroxy-4-dehydro-steroid and the 6$\beta$,7$\beta$-dihydroxy isomer thereof with the 3-keto-6$\beta$,7$\beta$-dihydroxy-4-dehydro-steroid perdominating, as determined by nuclear magnetic resonance spectroscopy.

By our invention we have also discovered that by converting a 3-keto-6$\beta$,7$\beta$-dihydroxy-4-dehydro-steroid to a 3-keto-6$\beta$,7$\beta$-diacyloxy ester derivative wherein said acyloxy group is a good leaving group (e.g. to a 3-keto-6$\beta$,7$\beta$-dimethanesulfonyloxy-4-dehydro-steroid) and by treating said 3-keto-6$\beta$,7$\beta$-diacyloxy-4-dehydrosteroid with an azide salt in a nonreactive organic solvent, there is obtained, in good yield, a 3-keto-6-azido-4,6-bis-dehydro-steroid, a known, pharmacologically active class of compounds. This is surprising, since we have also discovered that the epimeric 3-keto-6$\alpha$,7$\alpha$-diacyloxy-4-dehydro esters upon similar treatment with an azide salt do not produce 3-keto-6-azido-4,6-bis-dihydro-steroids and that similar treatment of the isomeric 3-keto-6$\beta$,7$\alpha$-diacyloxy-4-dehydro esters produces only difficultly separable product mixtures containing, at best, but a small amount of 3-keto-6-azido-4,6-bis-dehydro-steroid. Indeed, prior to our invention, the conversion of a 3-keto-6$\beta$,7$\beta$-disubstituted-4-dehydrosteroid to a 3-keto-6-substituted-4,6-bis-dehydro-steroid was unknown. Our invention thus provides a novel, convenient method for preparing valuable 3-keto-6-azido-4,6-bis-dehydro-steroids via novel 3-keto-6$\beta$,7$\beta$-diacyloxy-4-dehydro-steroidal intermediates.

SUMMARY OF INVENTION

In its process aspect, the invention sought to be patented resides in the concept of a method for the preparation of 3-keto-6-azido-4,6-bis-dehydro-steroids having pharmacological activity or being useful as intermediates, which comprises treating a 3-keto-6$\beta$,7-diacyloxy-4-dehydro-steroid wherein said acyloxy is a good leaving group with an azide salt in a nonreactive organic solvent.

A preferred method of this invention is the preparation of therapeutically valuable 3-keto-6-azido-4,6-pregnadienes, particularly of the corticoid series, by treatment of a 3-keto 6$\beta$,7$\beta$-dihydrocarbonsulfonyloxy-4-pregnene (preferably a 3-keto-6$\beta$,7$\beta$-dimethanesulfonyloxy-4-pregnene) with an alkali metal azide (preferably sodium azide) in a nonreactive, organic solvent.

A particularly valuable species of our prcess is that wherein the 3-keto-6$\beta$,7$\beta$-dihydrocarbonsulfonyloxy-4-dehydro-steroid intermediate is prepared by treating the corresponding 3-keto-4,6-bis-dehydro-steroid with osmium tetroxide followed by reductive cleavage of the thereby formed 6$\beta$,7$\beta$-osmate ester and thence esterifying the resulting 3-keto-6$\beta$,7$\beta$-dihydroxy-4-dehydro-steroid with a hydrocarbonsulfonyl halide in a tertiary amine.

In its composition-of-matter aspect, the invention sought to be patented resides in the concept of a 3-keto-6$\beta$,7$\beta$-dihydrocarbonsulfonyloxy-4-dehydro-steroid and their 6$\beta$,7$\beta$-dihydroxy precursors, useful intermediates in the process of the invention. Preferred species include 3-keto-6$\beta$,7$\beta$-dimethanesulfonyloxy-4-pregnenes of the corticoid series substituted at C-16.

GENERAL DESCRIPTION OF THE PROCESS OF THE INVENTION

According to our process, a 3-keto-6β,7—diacyloxy-4-dehydro-steroid wherein said acyloxy is a good leaving group is treated with an azide salt in a non-reactive, organic solvent, whereby is formed a 6-azido-4,6-bis-dehydro-steroid having pharmacological activity or being useful as an intermediate.

Azide salts useful as reagents in our process are known compounds and include quaternary ammonium azides (e.g. tetra-n-butylammonium azide) quaternary guanidinium azides (e.g. tetramethylguanidinium azide), alkaline earth metal azides (e.g. magnesium azide, calcium azide, barium azide) and, preferably, alkali metal azides (e.g. potassium azide, lithium azide, and preferably sodium azide).

Solvents suitable for use in this process are any non-reactive, organic solvent in which the starting 3-keto-6β,7—diacyloxy-4-pregnene and the azide reagent are soluble. The term "nonreactive" means any organic solvent which will not react with the steroid substrate or the azide reagent so as to cause transformations which will result in competing side reactions. When the azide reagent is an alkaline earth azide or an alkali metal azide, nonreactive solvents contemplated for use include hydroxylated hydrocarbons (e.g. methanol, ethanol, etc., as well as glycols such as ethyleneglycol-monomethyl ether), cyclic ethers (e.g. dioxane), dialkyl amides (e.g. dimethylformamide, etc.), hexaalkyl-phosphoramides (e.g. hexamethylphosphoramide), dialkyl sulfoxides (e.g. dimethylsulfoxide) and solvent mixtures such as dioxane-water, dioxane-water-ethanol, including solvent mixtures containing acetic acid, e.g. methanol-water-acetic acid which become buffered to a pH of about 6.5 when the azide salt reagent is added to the reaction mixture.

When converting a 3-keto-6β,7—-dihydrocarbonsulfonyloxy-1,4-bis-dehydro-steroid to a 3-keto-6-azido-1,4,6-tri-dehydro-steroid utilizing an alkaline earth or alkali metal azide by our process, particularly useful solvents are aprotic solvents such as dimethylsulfoxide, dimethylacetamide, dioxane, tetrahydrofurane, hexamethylphosphoramide, acetonitrile and, preferably, dimethylformamide. Aqueous solvent mixtures buffered to about pH 6.5 (e.g. aqueous methanol and acetic acid) are preferred, however, when treating a 3-keto-6β,7β-dihydrocarbonsulfonyloxy-1,2-dihydro-4-dehydro-steroid, particularly those having a 9α-halogeno group, with an azide reagent such as an alkaline earth metal or alkali metal azide according to our process, since these solvent mixtures minimize occurrences of competing side reactions due to enolization of the α,β-unsaturated-keto-system in the A-ring of the 3-keto-6β,7β-diacyloxy-1,2-dihydro-4-dehydro-steroid starting compound. When a quaternary ammonium salt (e.g. tetra-n-butyl-ammonium azide) or a quaternary guanidinium salt (e.g. tetramethylguanidinium azide) is used as azide reagent, the solvents of choice are halogenated hydrocarbons (e.g. methylene chloride, carbon tetrachloride, and chloroform), ethers (e.g. diethyl ether), cyclic ethers (e.g. dioxane), and hydroxylated hydrocarbons (e.g. methanol, ethanol).

As used in the specification and claims of this application, the term "acyl" denotes a radical derived from an organic or inorganic acid by removal of the hydroxyl group, e.g. trifluoroacetyl is the acyl radical of trifluoroacetic acid, methanesulfonyl is the acyl radical of methanesulfonic acid, and 2,4-dinitrobenzoyl is the acyl radical of 2,4-dinitrobenzoic acid.

According to our inventive concept, any 6β,7—diacyloxy groups which are good leaving groups present in a 3-keto-6β,7-diacyloxy-4-dehydro-steroid, upon treatment with an azide reagent in a nonreactive organic solvent, will undergo replacement and dehydroacyloxylation to produce a 3-keto-6-azido-4,6-bis-dehydro-steroid.

Acyl radicals of the requisite 3-keto-6β,7—-diacyloxy-4-dehydro-steroid starting compounds of our invention which form good acyloxy leaving groups preferably include those derived from hydrocarbonsulfonic acids having up to 12 carbon atoms such as dodecylsulfonic acid, ethanesulfonic acid, benzene sulfonic acid, mesitylsulfonic acid, p-toluenesulfonic acid and, particularly, methanesulfonic acid. Other good leaving groups contemplated are acyl radicals derived from hydrocarboncarboxylic acids wherein the carbon alpha to the carboxy group is substituted by an electron withdrawing group such as a fluorine, chlorine, bromine, nitro, cyano, carbomethoxy including 2,4-dinitrobenzoic acid, trifluoroacetic acid, cyanoacetic, p-fluorobenzoic acid and α-chloropropionic acid. In carrying out our process we prefer to use 3-keto-6β,7β-dimethanesulfonyloxy-4-dehydro-steroids as starting compounds.

Our process is usually carried out in a non-reactive, organic solvent at temperatures in the range of from about 0°C to about 80°C, preferably between about 20°C to about 50°C.

Our process is advantageously, but not necessarily, carried out in the absence of light under an inert atmosphere, e.g. nitrogen, argon, and the like.

Generally, when preparing a 3-keto-6-azido-4,6-bis-dehydro-steroid according to our process, the 3-keto-6β,7—diacyloxy-4-dehydro starting steroid (e.g. 6β,7β-di-methanesulfonyloxy-9α-fluoro-16α-methyl-1,4-pregnadiene-11β,17α,21-triol-3,20-dione 21-acetate) is added to a stirred suspension of the azide agent (e.g. an alkali metal azide such as sodium azide) in a nonreactive organic solvent (e.g. an aprotic solvent, preferably dimethylformamide), the quantities of azide reagent utilized ranging from 1 to 50 moles per mole of steroid. When an alkali metal azide or an alkaline earth metal azide in an aprotic solvent or in slightly acidic aqueous alkanol is used, large molar excesses of azide reagent are preferred; when a quaternary ammonium azide or a quaternary guanidinium azide in a halogenated solvent is used, a 10-molar excess of azide reagent is conveniently used.

The reaction is optimally carried out under an inert atmosphere (e.g. nitrogen) in the absence of light, at temperatures in the range of from about 20°C to about 80°C, usually at room temperature, until the replacement at C-6 and deacyloxylation at C-7(6) are complete as evidenced by thin layer chromatographic analysis. (Reaction time usually takes from about 18 to 24 hours.) The resulting 3-keto-6-azido-4,6-bis-dehydro-steroid is then isolated utilizing conventional techniques. In one method, the reaction mixture is poured into a large volume of water and the resulting insoluble fraction collected by filtration then dissolved in an organic solvent (e.g. chloroform); the resulting organic solvent solution is washed with water to remove inorganic impurities, then evaporated in vacuo at room temperature to a residue comprising the 3-keto-6-azido-4,6-bis-dehydro-steroid product (e.g. 6-azido- 9α-fluoro-16α-methyl-1,4,6-pregnatriene-11β,17α,21-triol-3,20-dione 21-acetate). Further purification may be effected by recrystallization and/or chromatography.

The process of our invention whereby a 3-keto-6β,7—diacyloxy-4-dehydro-steroid is substituted at C-6 by an azido function and dehydroacylated at C-7(6) is applicable to any steroid possessing a 3-keto-6β,7—diacyloxy-4-dehydro system wherein the 6β,7—diacyloxy- functions are good leaving groups, (e.g. hydrocarbonsulfonyloxy, particularly methanesulfonyloxy groups). Thus, any pregnane, androstane, cholestane, spirostane, ergostane, lanostane, stigmastane, saponin, sapogenin or bile acid, including their 19-nor analogs, which contains a 3-keto-6β,7—dihydrocarbonsylfonyloxy-4-dehydro system, will, upon treatment with an azide reagent in a nonreactive organic solvent, be converted to the corresponding 3-keto-6-azido-4,6-bis-dehydro derivative. Thus, 6β,7β-dihydrocarbonsulfonyloxy derivatives of 3-keto-4-pregnenes such as cortisone, hydrocortisone, prednisone, prednisolone and their 9α-fluoro derivatives, dexamethasone, betamethasone, triamcinolone, 16-methylene-17α-acetoxy-progesterone, 19-norprogesterone, and the like are converted to the corresponding 3-keto-6-azido-4,6-pregnadiene. Similarly, 6β,7β-dihydrocarbonsulfonyloxy derivatives of 3-keto-4-androstenes such as testosterone, 17α-ethinyl-19-nortestosterone, 4-androstene-3,17-dione are converted to the corresponding 6-azido-4,6-androstadiene.

Substituents present in the 3-keto-6β,7—diacyloxy-4-dehydro starting steroid of our process usually remain unchanged under the conditions of our process and, preferably, are present in the 6β,7—diacyloxy-4-dehydro-steroid intermediate prior to reaction with an azide salt according to our process. Thus, by way of example, the 3-keto-6β,7β-diacyloxy-4-dehydro starting steroids of our invention may be substituted at C-1 by a lower alkyl group; at C-9 by halogen, at C-11 by oxygen, hydroxyl, and halogen; at C-16 by lower alkyl, lower alkylidene or lower halogeno-alkylidene, halogen, hydroxy or alkanoyloxy; and at C-17 may have a 17-keto, 17β-hydroxyl, 17α-lower alkyl-17β-hydroxy, 17α-alkinyl-17β-hydroxy, 17α-halogenalkinyl-17β-hydroxygroupings as well as esters and derivatives of the foregoing, and also may have a sapogenin, cholestane, corticoid, progesterone or a 17α-substituted progesterone side chain.

In view of the use of osmium tetroxide in the preparation of the 6β,7β-dihydroxy-precursors of the 3-keto-6β,7β-diacyloxy-4-dehydro-steroid intermediates of this invention, substituents containing unsaturations, e.g. 16-alkylidene, 16-halogenoalkylidene, 17α-alkinyl-17β-hydroxy, and 17α-halogenoalkinyl-17β-hydroxy, are preferably introduced into the molecule after preparation of the 6β,7β-dihydroxy intermediate.

Preferred species of our process include the process of preparing pharmacologically active 6-azido-4,6-pregnadienes of the corticoid and progesterone series.

Included among the 6-azido-4,6-pregnadienes of the corticoid series prepared by our process are 6-azido-21-oxygenated-4,6-pregnadiene-3,20-diones of the following formula I:

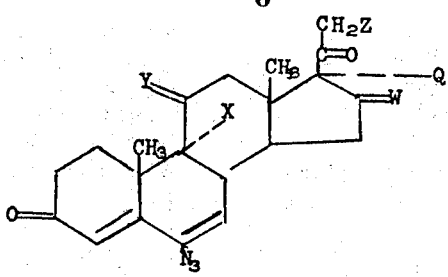

wherein Q is a member selected from the group consisting of hydrogen, hydroxy, and OR, R being an acyl radical of a hydrocarbon carboxylic acid having up to 12 carbon atoms;

W is a member selected from the group consisting of hydrogen (H,α-alkyl), (H,β-alkyl), (H,α-OH), (H,αOR') wherein R' is an acyl radical of a hydrocarbon carboxylic acid having up to 12 carbon atoms, =CHT wherein T is a member selected from the group consisting of hydrogen, alkyl, fluorine and chlorine, and W taken together with Q is 16α,17α-alkylidenedioxy;

X is a member selected from the group consisting of hydrogen and halogen having an atomic weight less than 100;

Y is a member selected from the group consisting of hydrogen, oxygen, (H,βOH), and, provided X is halogen, (H,β-halogen of atomic weight less than 100);

Z is a member selected from the group consisting of hydroxy, and OR'' wherein R'' is an acyl radical of an acid selected from the group consisting of a hydrocarbon carboxylic acid having up to 12 carbon atoms; and Z taken together with Q is a member selected from the group consisting of 17α,21-alkylidenedioxy and a 17α,21-alkylorthoalkanoate.

The alkyl groups included within the definition of the substituents W and T are preferably lower alkyl groups, i.e. radicals having usually up to four carbon atoms such as methyl, ethyl, n-propyl, iso-propyl, sec.-butyl, and tert.-butyl, although higher homologs such as pentyl and hexyl come within the scope of this invention.

The alkylidene groups of the compounds of above formula I are preferably lower alkylidenes, i.e. hydrocarbon radicals having preferably up to four carbon atoms and having a terminal double bond, including radicals such as methylene, ethylidene, n-propylidene, iso-propylidene, n-butylidene, sec.-butylidene, and the like. The 16-lower alkylidene derivatives of this invention (i.e. when W in above formula I is =CHT) are double bonded to the D-ring at C-16. The 16α,17α-alkylidenedioxy derivatives and the 17α,21-alkylidenedioxy derivatives have the alkylidene terminal bonds attached to different oxygen atoms, i.e. to to the oxygens at C-16 and C-17 in the case of the 16α,17α-alkylidenedioxy derivatives, or to the oxygens at C-17 and C-21 in the case of the 17α,21-alkylidenedioxy derivatives.

The compounds of formula I are conveniently prepared by our process by treating the corresponding 6β,7β-dimethanesulfonyloxy-4-pregnene with sodium azide in a nonreactive organic solvent. The thus prepared 6-azido-21-oxygenated compounds of formula I wherein Z is hydroxy, acyloxy, or together with Q at C-17 is a 17α,21-alkylidenedioxy, possess corticoid properties. Of these, the 6-azido-pregnanes unsubstituted at C-9 and C-11, i.e. those wherein X and Y are each hydrogen, e.g. 6-azido-16-W-17α-Q-4-pregnene-21-ol-3,20-diones of formula I possess mineralo-corticoid properties and, as such, are useful in the treatment of conditions requiring retention of sodium, e.g. adrenal insufficiency (i.e. Addison's disease) and salt losing syndromes.

Those 6-azido-21-oxygenated-4-pregnene-3,20-diones of formula I which have a halogen or an oxygen function at C-11 possess glucocorticoid activity and are particularly valuable as anti-inflammatory agents. Of these, preferred species are 6-azido-11,17-bis-oxygenated derivatives, particularly 6-azido-4,6-pregnadiene-17α,21-diol-3,20-diones of formula I and their 1-dehydro analogs wherein X is fluoro and Y is (H,βOH) or keto, including their ester and alkylidenedioxy derivatives. Of special interest in this group are compounds substituted at C-16 by an α-methyl, β-methyl or an α-hydroxy group or ester or alkylidene derivative thereof, which possess enhanced anti-inflammatory activity.

Illustrative of the pharmacologically active 6-azido-4,6-pregnadienes and 6-azido-1,4,6-pregnatrienes of formula I prepared by our process are the following:

6-azido-6-dehydrodexamethasone (i.e. 6-azido-9α-fluoro-16α-methyl-1,4,6-pregnatriene-11β,17α,21-triol-3,20-dione), a 1-dehydro compound of formula I wherein Q and Z are hydroxyl, X is fluorine, Y is (H,βOH) and W is (H,α-methyl) and the 21-acetate and 17,21-dipropionate esters thereof and the 1,2-dihydro analogs of the foregoing;

6-azido-6-dehydrobetamethansone (i.e. 6-azido-9α-fluoro-16β-methyl-1,4,6-pregnatriene-11β,17α,21-triol-3,20-dione) and the 21-acetate, and 17,21-dipropionate esters thereof and the 1,2-dihydro analogs of the foregoing;

6-azido-6-dehydro-triamcinolone (i.e. 6-azido-9α-fluoro-1,4,6-pregnatriene-11β,16α,17α,21-tetrol-3,20-dione), the 16,17-isopropylidene-21 acetate and 16,21-diacetate esters thereof and the 1,2-dihydro analogs of the foregoing;

6-azido-6-dehydroprednisolone (i.e. 6-azido-1,4,6-pregnatriene-11β,17α,21-triol-3,20-dione), the 9α-fluoro derivative thereof and their 21-acetate esters, and the 1,2-dihydro analogs of the foregoing;

6-azido-6-dehydroprednisone (i.e. 6-azido-1,4,6-pregnatriene-17α,21-diol-3,11,20-trione), the 9α-fluoro- and the 16β-methyl derivatives thereof and their 21-acetate esters and the 1,2-dihydro analogs of the foregoing.

The enhanced anti-inflammatory activity of 6-azido-4,6-bis-dehydropregnanes of formula I oxygenated at C-11, C-17 and C-21 are demonstrated by pharmacological tests in animals. Thus, for example, 6-azido-6-dehydrodexamethasone, when tested in the well-known granuloma pouch assay, demonstrates antiinflammatory activity which is about 1.5 times more active than that exhibited by 6-dehydrodexamethasone. Similarly, in the granuloma pouch assay 6-azido-6-dehydrobetamethasone has been found to be over three times as active as 6-dehydrobetamethasone as an anti-inflammatory agent.

In addition to the foregoing, 6-azido-9α-11β-dihalogeno-4,6-pregnadiene-17α,21-bis-oxygenated-compounds of formula I (especially the 17-mono and 17,21-di-lower alkanoate esters thereof) wherein X and Y are halogen, preferably those wherein the C-11 halogen (Y) is at least as electronegative as the C-9 halogen (X), topical anti-inflammatory agents include compounds such as:

6-Azido-9α,11β-dichloro-4,6-pregnadiene-17α,21-diol-3,20-dione, the 21-acetate thereof, the 17-monovalerate thereof, the 17α,21-di-propionate thereof, and the 17,21-iso-propylidene derivative thereof, and the 1-dehydro analogs of the foregoing;

6-Azido-9α,11β-dichloro-16α-hydroxy-4,6-pregnadiene-17α,21-diol-3,20-dione, the 16,21-diacetate thereof, and the 16α,17α-iso-propylidene thereof, and the 1-dehydro analogs of the foregoing;

6-Azido-9α,11β-dichloro-16α-methyl-4,6-pregnadiene-17α,21-diol-3,20-dione, the 17-propionate, the 17,21-dipropionate esters thereof and the 1-dehydro analogs of the foregoing;

6-Azido-9α,11β-dichloro-16β-methyl-4,6-pregnadiene-17α,21-diol-3,20-dione, the 17-propionate and 17,21-dipropionate esters thereof, and the 1-dehydro analogs of the foregoing.

Pharmacologically active 6-azido-6-dehydro steroids of the progesterone series which are conveniently prepared by our process include 6-azido-6-dehydroprogesterones of following formula II:

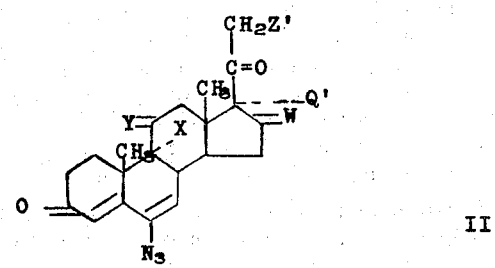

wherein W, X and Y are as defined hereinabove for formula I:

Q is a member selected from the group consisting of hydroxy, and OR, R being an acyl radical of a hydrocarbon-carboxylic acid having up to 12 carbon atoms, and hydrogen provided W is hydrogen or (H, lower alkyl); and Z' is a member selected from the groups consisting of hydrogen and halogen (preferably fluorine).

Compounds defined by formula II possess pharmacological and therapeutic properties.

In general, compounds of formula II, particularly those wherein X, Y, and Z' are hydrogen, exhibit progestational activity and may be used in conditions requiring a progestational agent. They are also useful in the treatment of disorders requiring antiandrogen therapy such as treatment of acne, or benign prostate hypertrophy. Included in this group of progestational agents are compounds such as 6-azido-17α-acetoxy-6-dehydroprogesterone and the 1-dehydro analog thereof (i.e. 6-azido-17α-acetoxy-4,6-pregnadiene-3,20-dione and the 1-dehydro analog thereof) which are prepared by our process from 6β,7β-dimethanesulfonyloxy-17α-acetoxy-4,6-pregnadiene-3,20-dione or of the 1-dehydro analog thereof by reaction with sodium azide in a nonreactive organic solvent (e.g. slightly acidic aqueous methanol when preparing the 6-azido-6-dehydro progesterone and dimethyl formamide when preparing the 6-azido-1,6-bis-dehydroprogesterone derivative).

Also prepared by our process are 6-azido-16-unsubstituted-17α-hydroxy-21-fluoro-6-dehydroprogesterones and 1-dehydro analogs thereof of formula II and the 16-lower alkyl analogs thereof which have topical anti-inflammatory activity such as:

6-Azido-9α,21-difluoro-4,6-pregnadiene-17α-ol-3,11,20-trione and the 16α-methyl and 16β-methyl analogs thereof;

6-Azido-9α,21-difluoro-4,6-pregnadiene-11β,17α-diol-3,20-dione and the 16α-methyl and 16β-methyl analogs thereof;

6-Azido-21-fluoro-4,6-pregnadiene-17α-ol-3,11,20-trione and the 16α-methyl and 16β-methyl analogs thereof;

6-Azido-21-fluoro-4,6-pregnadiene-17α-ol-3,20-dione and the 16α-methyl and 16β-methyl analogs thereof.

Also prepared by our process are the 1-dehydro-analogs of the above-listed 6-azido-17α-hydroxy-21-fluoro-6-dehydroprogesterone topical anti-inflammatory agents as well as the corresponding 21-unsubstituted derivatives which also exhibit anti-inflammatory activity. For example, 6β,7β-dimethanesulfonyloxy-9α-fluoro-16α-methyl-11β,17α-hydroxy-1-dehydroprogesterone upon reaction with sodium azide in dimethylformamide yields 6-azido-9α-fluoro-16α-methyl-11β,17α-dihydroxy-1,4,6-pregnatriene-3,20-dione which exhibits anti-inflammatory activity about six times that of prednisolone acetate when tested in the rat via the subcutaneous route by the granuloma pouch test.

Our process also provides a method for the preparation of 6-azido-4,6-androstadienes thereof such as those defined by following structural formula III and the 1-dehydro analogs thereof:

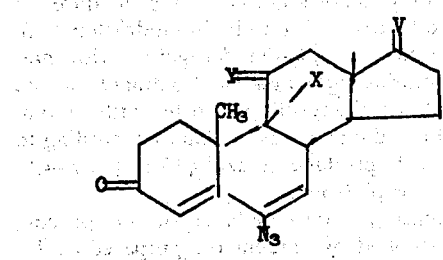

wherein X is a member selected from the group consisting of hydrogen and halogen;

Y is a member selected from the group consisting of hydrogen, oxygen, (H,βOH), and (H,β-halogen of atomic weight less than 100) provided X is halogen;

V is a member of the group consisting of oxygen, (H,β-OR'), (α-methyl,β-OR'), (α-lower alkinyl,β-OR') and (α-halogenoalkinyl,β-OR') wherein R' is a member selected from the group consisting of hydrogen and lower alkanoyl.

The 3-keto-6-azido-4,6-androstadienes of formula III are physiologically active substances, the 6-azido-17α-lower alkinyl- and the 6-azido-17α-lower halogenoalkinyl-4,6-androstadienes thereof having progestational activity, while the other 6-azido-4,6-androstadienes of formula III possess androgenic activity.

Typical 6-azido-4,6-androstadienes of formula III which may be prepared by our process include
- 6-azido-4,6-androstadiene-3,17-dione,
- 6-azido-4,6-androstadiene-17β-ol-3-one and the 17-lower alkanoates thereof,
- 6-azido-17α-methyl-4,6-androstadiene-17β-ol-3-one,
- 6-azido-17α-ethinyl-4,6-androstadiene-17β-ol-3-one and the 1-dehydro analogs of the foregoing;
- 6-azido-17α-chloroethinyl-4,6-androstadiene-17β-ol-3-one.

In addition to the foregoing, other 6-azido-4,6-bis-dehydro-steroids prepared by our process, such as those of the cholestane and sapogenin series are useful mainly as intermediates in processes involving degradation and/or rearrangement of the side chain at C-17 to produce therapeutically active 6-azido-4,6-bis-dehydro-steroids of the pregnane and androstane series such as those of formulae I, II and III described hereinabove.

GENERAL DESCRIPTION OF THE COMPOSITIONS-OF-MATTER OF THE INVENTION

The compositions-of-matter of this invention include 3-keto-6β,7β-dihydrocarbonsulfonyloxy-4-dehydro-steroids, necessary intermediates of the process of this invention and their 6β,7β-dihydroxy precursors.

The 3-keto-6β,7β-dihydroxy-4-dehydro-steroid precurosors are conveniently prepared from the corresponding 3-keto-6,7-unsubstituted 4,6-bis-dehydro-steroid by reaction thereof with osmium tetroxide in an aprotic solvent, preferably dioxane, whereby is prepared a mixture of the corresponding 6β,7β-dihydroxy-4-dehydro-steroid and the 6α,7α-dihydroxy-epimer thereof. Under the conditions of our osmylation process, the 6β,7β-dihydroxy epimer usually represents the major portion of the product mixture, particularly when the starting steroid has a 9α-halogeno-11β-hydroxy-system when isolatable quantities of the 6α,7α-dihydroxy isomer are not observed.

Osmium tetroxide is the preferred reagent for our process; however, other transition metal oxides may be used, such as the oxides of manganese, molybdenum, selenium, tungsten, chromium and titanium, particularly potassium permanganate, potassium molybdate, tungsten trioxide and tungstic acid.

We usually carry out our osmylation process under an inert atmosphere (e.g. nitrogen, argon, and the like) in the absence of light, in an aprotic solvent (e.g. dimethylsulfoxide, dimethylformamide, tetrahydrofuran and, preferably, dioxane) in the presence of a tertiary amine, e.g. pyridine.

The osmylation reaction may be carried out at temperatures in the range of from about 10°C to about 100°C and preferably at room temperature.

Generally, when preparing a 3-keto-6β,7β-dihydroxy-4-dehydro-steroidal intermediate, to a solution of a 3-keto-6,7-unsubstituted 4,6-bis-dehydro-steroid (e.g. 9α-fluoro-16β-methyl-1,4,6-pregnatriene-11β,17α,21-triol-3,20-dione 21-acetate) in dioxane to which pyridine has been added (2 ml. of pyridine per gram of osmium tetroxide) under an atmosphere of nitrogen at room temperature, there is added osmium tetroxide, the quantity of osmium tetroxide usually being equimolar to that of 3-keto-4,6-bis-dehydro-steroid. Alternatively, osmium tetroxide in catalytic amounts may be used together with other oxidizing agents such as hydrogen peroxide or N-methylmorpholine hydrogen peroxide complex. The reaction is continued until a thin layer chromatographic analysis of an aliquot indicates the absence of 6-dehydro starting steroid (usually 2.5 to 3 days). Hydrogen sulfide or another reductive cleavage agent is then added to the reaction mixture to split the intermediate osmate ester. The resultant precipitate of osmic sulfide is removed by filtration and the filtrate evaporated to a residue comprising a 3-keto-6β,7β-dihydroxy-4-dehydro-steroid (e.g. 6β,7β-dihydroxy-9α-fluoro-16β-methyl-1,4-pregnadiene-11β,17α,21-triol-3,20-dione 21-acetate). Purification is usually effected by recrystallization (for example, from chloroform-methanol) whereby, in the case of 9α-halogeno-11β-hydroxy-derivatives, the 6β,7β-dihydroxy compound usually precipitates first with any 6α,7α-dihydroxy isomer, which may be present (usually in trace quantities) remaining in the filtrate. When preparing a 9-unsubstituted derivative such as 6β,7β-dihydroxy-1,4,6-pregnatriene-11β,17α,21-triol-3,20-dione 21-acetate, upon recrystallization of the epimeric product mixture, the 6α,7α-dihydroxy epimer usually precipitates first and the 6β,7β-dihydroxy epimer is obtained upon further concentration of the recrystallizing solution or by adding additional solvent in which the 6β,7β-dihydroxy isomer is less soluble. Other methods known in the art of purifying and separating the isomeric mixture of 6β7β-and 6α,7α-dihydroxy-4-dehydro-steroidal intermediates may also be used such as thick layer and column chromatography with like fractions (as determined by thin layer chromatography) being combined.

The 3-keto-6β,7β-dihydroxy-4-dehydro-steroidal intermediates of our invention are usually white crystalline solids which are soluble in most organic solvents and insoluble in water.

The 3-keto-6β,7β-dihydroxy-4-dehydro-steroid intermediates are converted to their 6β,7β-dihydrocarbonsulfonyl esters by treatment with a hydrocarbonsulfonyl halide having up to 12 carbon atoms in a basic medium, preferably pyridine, or alternatively, where the basic medium is provided by an alkali metal bicarbonate in an inert solvent, e.g. sodium bicarbonate in acetone.

Generally, the esterification is carried out in basic media under relatively mild conditions known to esterify secondary hydroxyl groups, preferably, at room temperature in pyridine utilizing large molar excesses of an acid halide of a hydrocarbon-sulfonic acid (e.g. p-toluenesulfonyl chloride or methanesulfonyl chloride).

Acyl radicals which form good leaving acyloxy groups are derived from hydrocarbonsulfonic acids having up to 12 carbon atoms including methanesulfonic acid, ethanesulfonic acid, benzenesulfonic acid, p-toluenesulfonic acid, mesitylsulfonic acid and dodecylsulfonic acid.

The 3-keto-6,7-unsubstituted-4,6-bis-dehydro precursors of the 3-keto-6β,7β-dihydroxy-4-dehydrosteroid intermediates of this invention are a known class of compounds conveniently derived from the corresponding 6,7-dihydro analogs by procedures known to effect dehydrogenation between C-6 and C-7, such as those utilizing chloranil or 2,3-dichloro-5,6-dicyanobenzoquinone (DDQ). When the starting steroid has a 16-alkyl substituent, e.g. 9α-fluoro-16β-methyl-1,4-pregnadiene-11β,17α,21-triol-3,20-dione 21-acetate, in order to minimize the possibility of rearrangement reactions, introductions of the 6-dehydro bond is preferably effected by the use of 2,3-dichloro-5,6-dicyanobenzoquinone in the presence of acid (e.g. DDQ in dioxane and hydrochloric acid).

Generally, when making the 3-keto-6β,7β-dihydroxy-4-dehydro-steroidal precursors of our invention, it is preferable to have all the substituents desired in the 6-azido-6-dehydro-steroid prepared by the novel process of our invention present in the 3-keto-4,6-bis-dehydro-steroid from whence the 6β,7β-dihydroxy compounds are derived. Alternatively, and preferably in the case of intermediates having substituents containing unsaturations such as 16-alkylidene or 17α-alkinyl derivatives, the unsaturated substituents may be added into 3-keto-6β, 7β-dihydroxy-4-dehydro-steroid intermediate or di-ester thereof utilizing procedures known in the art prior to treatment with sodium azide according to our process. Thus, 3-keto-6β,7β-dihydroxy-16-methylene-4-dehydro-steroidal intermediates are prepared from the corresponding 16β-methyl-16α,17α-oxido intermediates (e.g. 6β,7β-dihydroxy-16β-methyl-16α,17α-oxido-1,4-pregnadiene-21-ol-3,20-dione 21-acetate) by known methods (e.g. with hydrogen bromide in acetic acid) to produce 3-keto-6β, 7β-hydroxy-16-methylene-17α-hydroxy-steroidal intermediates (e.g. 6β,7β-dihydroxy-16-methylene-1,4-pregnadiene-17α,21-diol-3,20-dione 21-acetate) which upon esterification with methanesulfonylchloride followed by treatment of the resulting 6β,7β-dimethanesulfonyloxy derivative with an azide salt in an aprotic solvent according to our invention, yields a 6-azido-16-methylene-1,4,6-tri-dehydro-steroid (e.g. 6-azido-16-methylene-1,4-pregnatriene-17α,21-diol-3,20-dione 21-acetate).

Similarly, when preparing a 6β,7β-dimethanesulfonyloxy-4-androstene intermediate containing 17α-ethinyl-17β-hydroxyl-substituents, it is preferable to first prepare 6β,7β-dihydroxy-4-androstene-3,17-dione by osmylation of 4,6-androstadiene-3,17-dione and thence treat the 6β,7β-dihydroxy-17-keto-intermediate with sodium ethinyl according to known procedures to obtain 6β,7β-dihydroxy-17α-ethinyl-4-androsten-17β-ol-3-one. Esterification of the foregoing with methanesulfonylchloride followed by treatment of the resulting 6β,7β-dimethanesulfonate ester with sodium azide in slightly acidic aqueous methanol according to our process will produce 6-azido-17α-ethinyl-4,6-androstadiene-17β-ol-3-one.

The 6β,7β-diacyloxy intermediates of our process and their 6β,7β-dihydroxy precursors prepared as described above include compounds corresponding to the 6-azido-6-dehydro-steroids of above formula I, II, and III, but having a 6β,7β-dihydro-carbonsulfonyloxy (or dihydroxy)-6,7-dihydro system instead of a 6-azido-6-dehydro system as shown in formulae I, II and III. Of our intermediates, a preferred group are 6β,7β-diacyloxy-4-dehydro-steroids of the pregnane series, particularly those having a cortical side chain at C-17 and an oxygen function at C-11, a particularly preferred group being those having a 9α-halogeno-11β-hydroxy (or 11-keto)-system and a substituent at C-16, e.g. 16α-methyl, 16β-methyl, 16α-hydroxy, 16α-lower alkanoyloxy, or a 16α,17α-alkylidenedioxy, since such intermediates lead to corticoids having greatly enhanced activity over that of the 6-unsubstituted corticoids as discussed hereinabove. Included among this preferred group of intermediates are compounds of the following formula IV and their 1-dehydro analogs:

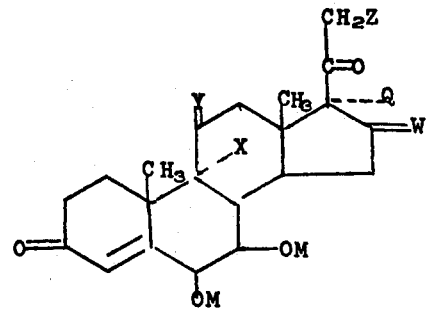

IV wherein M is a member selected from the group consisting of hydrogen and an acyl radical of a hydrocarbonsulfonic acid having up to 12 carbon atoms;

Q is a member selected from the group consisting of hydrogen, hydroxy and OR, R being an acyl radical of a hydrocarboncarboxylic acid having up to 12 carbon atoms;

W is a member selected from the group consisting of

(H,α-lower alkyl), (H,β-lower alkyl), (H,α-OH), (H,α-OR) wherein R is as defined hereinabove, =CHT when Q is other than hydrogen wherein T is a member selected from the group consisting of hydrogen, lower alkyl, fluorine and chlorine, and W and Q together represent an alkylidenedioxy derivative;

X is a member selected from the group consisting of hydrogen and a halogen having an atomic weight less than 100;

Y is a member selected from the group consisting of oxygen, (H,βOH),

provided X is hydrogen, and (H,β-halogen of atomic weight less than 100) provided X is halogen;

Z is a member selected from the group consisting of hydroxy, OR" (R" being an acyl radical of a hydrocarboncarboxylic acid having up to 12 carbon atoms), hydrogen, halogen, and Z together with Q is alkylidenedioxy derivative;

with the proviso that M is an acyl radical of a hydrocarbonsulfonic acid when W is

X is hydrogen, Y is oxygen and Z is OR" or when W is

X is fluorine, Y is (H,βOH) and Z is OR".

As discussed hereinabove, a particularly useful group of intermediates, because they lead to 6-azido-4,6-pregnadienes having enhanced anti-inflammatory activity, are compounds defined by formula IV wherein M is methanesulfonyl, Q is hydroxy or lower alkanoyloxy, X is fluorine, Y is (H,βOH), or keto, Z is lower alkanoyloxy, and W is (H,β-methyl), (H,α-methyl), (H,α-hydroxy) and (H,α-lower alkanoyloxy), including the (16,17), and (17,21) acetonide derivatives thereof, and the 1-dehydro analogs thereof.

Typical intermediates of our invention include compounds such as 6β,7β-dimethanesulfonyloxy-9α-fluoro-16α-methyl-1,4-pregnadiene-11β,17α,21-triol-3,20-dione 21-acetate, the 16β-methyl epimer thereof, and the corresponding 1,2-dihydro analogs of the foregoing;

6β,7β-dimethanesulfonyloxy-9α-fluoro-16α,17α-isopropylidenedioxy-1,4-pregnadiene-11β,21-diol-3,20-dione 21-acetate and the 1,2-dihydro analog thereof;

6β,7β-dimethanesulfonyloxy-9α-fluoro-16α-methyl-1,4-pregnadiene-11β,17α,21-triol-3,20-dione 17,21-dipropionate, the 16β-epimer thereof, and the corresponding 1,2-dihydro analogs of the foregoing.

6β,7β-dimethanesulfonyloxy-9α-fluoro-16α-methyl-1,4-pregnadiene-17α,21-diol-3,11,20-trione 21-acetate, the 16β-methyl epimer thereof, and the 1,2-dihydro analogs of the foregoing;

6β,7β-dimethanesulfonyloxy-9α-fluoro-1,4-pregnadiene-11β,16α,17α,21-tetrol-3,20-dione 16,21-diacetate and the 1,2-dihydro analog thereof;

6β,7β-dimethanesulfonyloxy-1,4-pregnadiene-11β,17α,21-triol-3,20-dione 21-acetate, the 9α-fluoro derivative thereof and the 1,2-dihydro analogs of the foregoing;

6β,7β-dimethanesulfonyloxy-1,4-pregnadiene-17α,21-diol-3,11,20-trione-21-acetate, the 9α-fluoro derivative thereof and the 1,2-dihydro analogs of the foregoing;

6β,7β-dimethanesulfonyloxy-17α-acetoxy-1,4-pregnadiene-3,20-dione and the 1,2-dihydro analog thereof; and 6β,7β-dimethanesulfonyloxy-9α-fluoro-16α-methyl-1,4-pregnadiene-11β,17α-diol-3,20-dione, the 16β-methyl epimer thereof, and the 1,2-dihydro analogs of the foregoing.

The methods of carrying out our inventive process are illustrated in the examples which follow. The scope of our invention, however, is not to be construed as limited by the specific embodiments described herein since obvious modifications of our process will be suggested by these examples and the teaching in the specification to one skilled in the art, and it is to be understood that these obvious modifications are encompassed within inventive concept. Thus, treatment of any 3-keto-6β,7—di-substituted-4-dehydro-steroid having substituents at C-6 and C-7 which are good leaving groups, e.g. 6β,7β-di-halogeno groups, with an azide salt according to our invention will produce a 3-keto-6-azido-4,6-bis-dehydro-steroid and thus is considered an equivalent of the process specifically defined and claimed herein.

Other good leaving groups contemplated as substituents at C-6 and C-7 for the intermediates of this invention are 6β,7β-diacyl derivatives of the 6β,7β-dihydroxy intermediates of formula IV wherein the acyl group is derived from a hydrocarbon carboxylic acid having up to twelve carbon atoms wherein the carbon alpha to the carboxy group is substituted by or is an integral part of an electron withdrawing group, e.g. acyl radicals of naphthoic acids, trifluoroacetic acid, 2,4-dinitrobenzoic acid, cyanoacetic acid and the like.

EXAMPLE 1

6-Azido-9α-fluoro-16α-methyl-1,4,6-pregnatriene-11β,17α,21-triol-3,20-dione(6-azido-6-dehydrodexamethasone)

A.

9α-Fluoro-16α-methyl-1,4,6-pregnatriene-11β,17α,21-triol-3,20-dione 21-acetate

To a solution of 42 g. of dry hydrogen chloride in 1.26 liters of dioxane at room temperature, add with stirring 20 g. of 9α-fluoro-16α-methyl-1,4-pregnadiene-11β,17α,21-triol-3,20-dione 21-acetate and 12.6 g. of 2,3-dichloro-5,6-dicyanobenzoquinone (hereinafter identified as DDQ). Stir at room temperature for 20 hours, then filter the resultant precipitate and wash the precipitate with dioxane. Evaporate the combined filtrates at room temperature in vacuo to a residue comprising 9α-fluoro-16α-methyl-1,4,6-pregnatriene-11β,17α,21-triol-3,20-dione 21-acetate. Purify by dissolving the residue in chloroform and chromatograph on a column of alumina grade V (300 g.). Wash the alumina column with 1.5 liters of chloroform, then evaporate the combined chloroform filtrates in vacuo to a residue. Crystallize the residue from hexane-methanol to give 9α-fluoro-16α-methyl-1,4,6-pregnatriene-11β,17α,21-triol-3,20-dione 21-acetate. Yield = 13.2 g., 65% theoretical yield.

B. 6β,7β-Dihydroxy-9α-fluoro-16α-methyl-1,4-pregnadiene-11β,17α,21-triol-3,20-dione 21-acetate To a solution of 7.65 g. of 9α-fluoro-16α-methyl-1,4,6-pregnatriene-11β,17α,21-triol-3,20-dione 21-acetate in 150 ml. of dioxane and 9 ml. of pyridine under an atmosphere of nitrogen and at room temperature, add 4.5 g. of osmium tetroxide. Stir the reaction mixture under an atmosphere of nitrogen at room temperature in the dark for 2.5 days, then saturate the reaction mixture containing the thus formed 6β,7β-osmate ester with hydrogen sulfide and stir for 3 hours. Filter the resultant precipitate and wash with dioxane. Evaporate the combined filtrate and washings at room temperature in vacuo to a residue. Wash the residue with chloroform and methanol and then crystallize from chloroform-methanol to give 6β,7β-dihydroxy-9α-fluoro-16α-methyl-1,4-pregnadiene-11β,17α,21-triol-3,20-dione 21-acetate. Yield = 4.6 g., 56% theoretical yield. Evaporate the washings from the crystallizations and purify the residue on a column of silica gel to obtain additional product (0.3 g.); m.p.=270°–274°C; $[\alpha]_D^{25}$ + 34.8° (dimethylformamide); $\lambda_{max}^{methanol}$ 239 nm ($\epsilon$=14,400); n.m.r. (dmso-$d_6$/$D_2O$)δ0.90($C_{13}$–$CH_3$); 1.63($C_{10}$–$CH_3$); 0.80($C_{16}$–$CH_3$; d,J7Hz); 3.56(7α -H;mult); 4.10(11α-H;mult); 4.26(6α-H;d,J4Hz); 6.18($C_4$-H); 6.26($C_2$-H;d,d J10,2Hz); 7.31($C_1$-H;d,J10Hz).

C. 6β,7β-Dimethanesulfonyloxy-9α-fluoro-16α-methyl-1,4-pregnadiene-11β,17α,21-triol-3,20-dione 21-acetate To a solution of 3 g. of 6β,7β-dihydroxy-9α-fluoro-16α-methyl-1,4-pregnadiene-11β,17α,21-triol-3,20-dione 21-acetate in 60 ml. of dry pyridine, add with stirring 6 ml. of methanesulfonyl chloride. Stir the reaction mixture at room temperature for 2 hours then pour into ice water and stir for an additional hour. Extract the aqueous reaction mixture with three portions of methylene chloride then wash the combined organic extracts with two portions of water. Dry the organic extracts over anhydrous magnesium sulfate then evaporate the dried organic extracts at room temperature in vacuo to a residue comprising 6β,7β-dimethanesulfonyloxy-9α-fluoro-16α-methyl-1,4-pregnadiene-11β,17α,21triol-3,20-dione 21-acetate, which is used without further purification in Example 1D immediately following.

D. 6-Azido-9α-fluoro-16α-methyl-1,4,6-pregnatriene-11β,17α,21-triol-3,20-dione 21-acetate Add the 6β,7β-dimethanesulfonyloxy-9α-fluoro-16α-methyl-1,4-pregnadiene-11β,17α,21-triol-3,20-dione 21-acetate (3.8 g.) prepared in Example 1C to a stirred suspension of 16 g. of sodium azide in 60 ml. dry dimethylformamide. Stir the reaction mixture under an atmosphere of nitrogen at room temperature in the absence of light for 24 hours, then pour the reaction mixture into water and filter off the resultant precipitate. Extract the filtrate with two portions of chloroform. Add the chloroform extracts to the filtered solid. Wash the chloroform solution of the filtered solid with three portions of water. Dry the chloroform solution over anhydrous magnesium sulfate and evaporate in vacuo at room temperature to a residue comprising 6-azido-9α-fluoro-16α-methyl-1,4,6-pregnatriene-11β,17α,21-triol-3,20-dione 21-acetate. Purify by preparative thick layer chromatography on silica gel or on a column of silica gel eluting with chloroform-ethyl acetate (3:1). Combine the like fractions and evaporate these combined eluates to a residue comprising 6-azido-9α-fluoro-16α -methyl-1,4,6-pregnatriene-11β,17α,21-triol-3,20-dione 21-acetate. Yield =1.4 g. 45% theoretical yield. This product is used without further purification in Example 1E following.

E. 6-Azido-9α-fluoro-16α-methyl-1,4,6-pregnatriene-11β,17α,21-triol-3,20-dione To a solution of 0.31 g. of 6-azido-9α-fluoro-16α-methyl-1,4,6-pregnatriene-11β,17α,21-triol-3,20-dione 21-acetate in 54 ml. of methanol, add 6 ml. of saturated aqueous sodium bicarbonate. Stir at room temperature under an atmosphere of nitrogen in the absence of light for 2 hours. Filter and wash the filtrate with methanol, then evaporate the combined organic filtrate and washings in vacuo at room temperature. Dissolve the resultant residue in ethyl acetate and wash the ethyl acetate solution with three portions of water. Dry the ethyl acetate solution over anhydrous magnesium sulfate and evaporate the ethyl acetate solution in vacuo at room temperature to a residue comprising 6-azido-9α-fluoro-16α-methyl-1,4,6-pregnatriene-11β,17α,21-triol-3,20-dione. (Yield=0.225 g.). Purify by crystallization from hexane-ether-methanol: m.p.=160°C (decomp.); $[\alpha]_D^{methanol}$ + 52.3°; $\lambda_{max}^{methanol}$ 249 mμ ($\epsilon$=16,000), 312 mμ ($\epsilon$ = 7,100).

EXAMPLE 2

6-Azido-9α-fluoro-16β-methyl-1,4,6-pregnatriene-11β,17α,21-triol-3,20-dione
(6-Azido-6-dehydrobetamethasone)

A. 9α-Fluoro-16β-methyl-1,4,6-pregnatriene-11β,17α,21-triol-3,20-dione 21-acetate In a manner similar to that described in Example 1A, treat 20 g. of 9α-fluoro-16β-methyl-1,4-pregnadiene-11β,17α,21-triol-3,20-dione 21-acetate with 12.6 g. of DDQ in 1.35 liters of dioxane containing 42 g. of dry hydrogen chloride. Isolate and purify the resultant product in a manner similar to that described in Example 1A to give 9α-fluoro-16β-methyl-1,4,6-pregnatriene-11β,17α,21-triol-3,20-dione 21-acetate. Yield = 11.1 g., 55% theoretical yield.

B.
6β,7β-Dihydroxy-9α-fluoro-16β-methyl-1,4-pregnadiene-11β,17α,21-triol-3,20-dione 21-acetate In a manner similar to that described in Example 1B, treat 3.4 g. of 9α-fluoro-16β-methyl-1,4,6-pregnatriene-11β,17α,21-triol-3,20-dione 21-acetate with 2 g. of osmium tetroxide in dioxane, followed by treatment with hydrogen sulfide of the osmate ester thus produced. Isolate and purify the resultant product in a manner similar to that described in Example 1B to obtain 6β,7β-dihydroxy-9α-fluoro-16β-methyl-1,4-pregnadiene-11β,17α,21-triol-3,20-dione 21-acetate. Yield = 2.2 g. 61% theoretical yield; m.p. = 243°–248°C; $[\alpha]_D^{25°}$ + 57.7 (dimethylformamide); $\lambda_{max}^{methanol}$ 240 nm ($\epsilon$=14,800); n.m.r. (dmso-$d_6$/$D_2O$) δ 0.95 ($C_{13}$-$CH_3$); 1.00 ($C_{16}$-$CH_3$; d,J7Hz); 1.63 ($C_{10}$-$CH_3$); 3.58 (7α-H;mult); 4.16 (11α-H;mult); 4.27(6α-H; d,J4Hz); 6.15 ($C_4$-H); 6.23 ($C_2$-H;d,d J10,2Hz); 7.27 ($C_1$-H; d,J 10Hz).

C.
6β,7β-Dimethanesulfonyloxy-9α-fluoro-16β-methyl-1,4-pregnadiene-11β,17α,21-triol-3,20-dione 21-acetate.

In a manner similar to that described in Example 1C, treat 3 g. of 6β,7β-dihydroxy-9α-fluoro-16β-methyl-1,4-pregnadiene-11β,17α,21-triol-3,20-dione 21-acetate with 6 ml. of methanesulfonyl chloride in 60 ml. of pyridine. Isolate and purify the resultant product in a manner similar to that described in Example 1C to obtain 6β,7β-dimethanesulfonyloxy-9α-fluoro-16β-methyl-1,4-pregnadiene-11β,17α,21-triol-3,20-dione 21-acetate, which is used without further purification in Example 2D following.

D.
6-Azido-9α-fluoro-16β-methyl-1,4,6-pregnatriene-11β,17α,21-triol-3,20-dione 21-acetate In a manner similar to that described in Example 1D, treat the 6β,7β-dimethanesulfonyloxy-9α-fluoro-16β-methyl-1,4-pregnadiene-11β,17α,21-triol-3,20-dione 21-acetate prepared in Example 2C with 16 g. of sodium azide in 50 ml. of dimethyl-formamide. Isolate and purify the resultant product in a manner similar to that described in Example 1D to obtain 1.5 g. of 6-azido-9α-fluoro-16β-methyl-1,4,6-pregnatriene-11β,17α,21-triol-3,20-dione 21-acetate.

E.
6-Azido-9α-fluoro-16β-methyl-1,4,6-pregnatriene-11β,17α,21-triol-3,20-dione In a manner similar to that described in Example 1E treat the 6-azido-9α-fluoro-16β-methyl-1,4,6-pregnatriene-11β,17α,21-triol-3,20-dione 21-acetate prepared in Example 2D with 39 ml. of saturated aqueous sodium bicarbonate and 360 ml. of methanol. Isolate and purify the resultant product in a manner similar to that described to obtain 1.12 g. (75% theoretical yield) of 6-azido-9α-fluoro-16β-methyl-1,4,6-pregnatriene-11β,17α,21-triol-3,20-dione. Purify by recrystallization from hexane-methanol m.p.=140°C (decomp.); $[\alpha]_D^{26°}$ +56.2°(dimethylformamide); $\lambda_{max}^{methanol}$ 248 nm ($\epsilon$=16,100), 312 nm ($\epsilon$=7,600).

EXAMPLE 3
6-Azido-9α-fluoro-16α,17α-iso-propylidenedioxy-1,4,6-pregnatriene-11β,21-diol-3,20-dione 21-acetate
(6-Azido-6-dehydrotriamcinolone-acetonide 21-acetate)

A.
9α-Fluoro-16α,17α-iso-propylidenedioxy-1,4,6-pregnatriene 11β,21-diol-3,20-dione 21-acetate In a manner similar to that described in Example 1A, treat 9α-fluoro-16α,17α-iso-propylidenedioxy-1,4-pregnadiene-11β,21-diol-3,20-dione 21-acetate (1 g.) with 0.48 g. of DDQ and 2 g. of dry hydrogen chloride in 30 ml. of dioxane. Isolate and purify the resultant product in a manner similar to that described in Example 1A to obtain 0.83 g. (85% theoretical yield) of 9α-fluoro-16α,17α-iso-propylidenedioxy-1,4,6-pregnatriene-11β,21-diol-3,20-dione 21-acetate; m.p. 280°–283°C; $[\alpha]_D^{26°}$ + 63.8 (chloroform); $\lambda_{max}^{methanol}$ 220 nm ($\epsilon$=12,400), 248 nm ($\epsilon$=9,700), 296 nm ($\epsilon$=12,500).

B.
6β,7β-Dihydroxy-9α-fluoro-16α,17α-iso-propylidenedioxy-1,4-pregnadiene-11β,21-diol-3,20-dione 21-acetate In a manner similar to that described in Example 1B, treat 9α-fluoro-16α,17α-iso-propylidenedioxy-1,4,6-pregnatriene-11β,21-diol-3,20-dione 21-acetate with osmium tetroxide in dioxane followed by treatment with hydrogen sulfide of the osmate ester thus produced and isolation of the resultant product to obtain 6β,7β-dihydroxy-9α-fluoro-16α,17α-iso-propylidenedioxy-1,4-pregnadiene-11β,21-diol-3,20-dione 21-acetate.

This product is used without further purification in the step immediately following.

C.
6β,7β-Dimethanesulfonyloxy-9α-fluoro-16α,17α-iso-propylidenedioxy-1,4-pregnadiene-11β,21-diol-3,20-dione 21-acetate In a manner similar to that described in Example 1C treat 388 mg. of 6β,7β-dihydroxy-9α-fluoro-16α,17α-iso-propylidenedioxy-1,4-pregnadiene-11β,21-diol-3,20-dione 21-acetate with 0.5 ml. of methanesulfonyl chloride in 5 ml. of pyridine to obtain 6β,7β-dimethanesulfonyloxy-9α-fluoro-16α,17α-iso-propylidenedioxy-1,4-pregnadiene-11β,21-diol-3,20-dione 21-acetate.

This product is used without further purification in Example 3D immediately following.

D.
6-Azido-9α-fluoro-16α,17α-iso-propylidenedioxy-1,4,6-pregnatriene-11β,21-diol-3,20-dione 21-acetate Treat the 6β,7β-dimethanesulfonyloxy ester prepared in the preceding Example 3C with 1.2 g. of sodium azide in 1.5 ml. of dimethylformamide in a manner similar to that described in Example 1D. Isolate and purify the resultant product in a manner similar to that described in Example 1D to obtain 47 mg. (12% theoretical yield) of 6-azido-9α-fluoro-16α,17α-iso-propylidenedioxy-1,4,6-pregnatriene-11β,21-diol-3,20-dione 21-acetate; $\lambda_{max}^{methanol}$ 246 nm ($\epsilon$=15,900), 307 nm ($\epsilon$=6,800).

EXAMPLE 4

6-Azido-9α-fluoro-16α-methyl-1,4,6-pregnatriene-11β,17α,21-triol 3,20-dione 17,21-dipropionate (6-Azido-6-dehydro-dexamethasone 17,21-dipropionate)

A.

9α-Fluoro-16α-methyl-1,4,6-pregnatriene-11β,17α,21-triol 3,20-dione 17,21-dipropionate In a manner similar to that described in Example 1A, treat 11.67 g. of 9α-fluoro-16α-methyl-1,4-pregnadiene-11β,17α,21-triol-3,20-dione 17,21-dipropionate with 6.34 g. of DDQ in a solution of 25 g. of dry hydrogen chloride in 750 ml. of dioxane to obtain 6.86 g. (60% theoretical yield) of 9α-fluoro-16α-methyl-1,4,6-pregnatriene-11β,17α,21-triol-3,20-dione 17,21-dipropionate; m.p. 167°–168.5°C; $[\alpha]_D^{26°}$ −14.4° (chloroform); $\lambda_{max}^{methanol}$ 220 nm ($\epsilon$=12,200), 250 nm ($\epsilon$=9,100), 297 nm ($\epsilon$=12,400).

B.

6β,7β-dihydroxy-9α-fluoro-16α-methyl-1,4-pregnadiene-11β,17α,21-triol-3,20-dione 17,21-dipropionate In a manner similar to that described in Example 1B, treat 5.9 g. of 9α-fluoro-16α-methyl-1,4,6-pregnatriene-11β,17α,21-triol-3,20-dione 17,21-dipropionate with 3 g. of osmium tetroxide in dioxane followed by treatment of the osmate ester thus produced with hydrogen sulfide and isolation of the resultant product to obtain 5.4 g. (85% theoretical yield) of 6β,7β-dihydroxy-9α-fluoro-16α-methyl-1,4-pregnadiene-11β,17α,21-triol-3,20-dione 17,21-dipropionate; m.p. = 143°C; $[\alpha]_D^{26°}$ −1.9° (chloroform); $\lambda_{max}^{methanol}$ 2.40 nm ($\epsilon$=12,900); n.m.r. (CDCl$_3$) δ 1.71 (C$_{10}$-CH$_3$); 3.88 (7α-H; mult); 4.45 (6αH+11α-H; mult); 6.25 (C$_4$-H); 6.30 (C$_2$-H;d,d J10,2Hz); 7.19 (C$_1$-H; d,J10Hz).

C.

6β,7β-dimethanesulfonyloxy-9α-fluoro-16α-methyl-1,4-pregnadiene-11β,17α,21-triol-3,20-dione-17,21-dipropionate Treat 1 g. of 6β,7β-dihydroxy-9α-fluoro-16α-methyl-1,4-pregnadiene-11β,17α,21-triol-3,20-dione 17,21-dipropionate with 2 ml. of methanesulfonyl chloride in 20 ml. of pyridine in a manner similar to that described in Example 1C to obtain 6β,7β-dimethanesulfonyloxy-9α-fluoro-16α-methyl-1,4-pregnadiene-11β,17α,21-triol-3,20-dione 17,21-dipropionate which is used without further purification in the step immediately following.

D.

6-Azido-9α-fluoro-16α-methyl-1,4,6-pregnatriene-11β,17α,21-triol-3,20-dione 17,21-dipropionate Treat the 6β,7β-dimethanesulfonyl product of the preceding paragraph with 3.6 g. of sodium azide in 10 ml. of dimethylformamide in a manner similar to that described in Example 1D to obtain 220 mg. (20% theoretical yield) of 6-azido-9α-fluoro-16α-methyl-1,4,6-pregnatriene-11β,17α,21-triol-3,20-dione 17,21-dipropionate. Purify by crystallization from ether-methanol; m.p. = 190°C (decomp.) $[\alpha]_D^{26°}$ + 13.1°(dimethylformamide); $\lambda_{max}^{methanol}$ 248 nm ($\epsilon$=16,450); 311 nm ($\epsilon$=6,900).

EXAMPLE 5

6-Azido-9α-fluoro-16β-methyl-1,4,6-pregnatriene-11β,17α,21-triol-3,20-dione 17,21-dipropionate A. (1) To 0.4 g. of 6-azido-9α-fluoro-16β-methyl-1,4,6-pregnatriene-11β,17α,21-triol-3,20-dione in 4 ml. of dimethylsulfoxide, add 0.9 ml. of tri-n-butylorthopropionate and 30 mg. of p-toluenesulfonic acid. Stir the reaction mixture at room temperature for four hours, then pour into water. Filter off the resultant precipitate, wash with water, then dry to give 0.46 g. of 6-azido-9α-fluoro-16β-methyl-1,4,6-pregnatriene-11β,17α,21-triol-3,20-dione 17,21orthopropionate.

2. Dissolve the 17,21-orthopropionate ester prepared in above Procedure 5A(1) in 12 ml. of acetic acid and 0.24 ml. of water. Stir the reaction mixture at room temperature for one hour, pour into 200 ml. of water, add 10% aqueous sodium bicarbonate solution until the reaction mixture is about pH 7, then extract the solution with two portions of ethyl acetate. Wash the combined organic extracts with three portions of water, then dry over anhydrous magnesium sulfate and evaporate at room temperature in vacuo to a residue comprising 0.43 g. of 6-azido-9α-fluoro-16β-methyl-1,4,6-pregnatriene-11β,17α,21-triol-3,20-dione 17-propionate.

3. Treat the 17-propionate ester prepared in above Example 5A(2) with 0.87 ml. of propionic anhydride and 8.7 ml. of pyridine at room temperature for 18 hours. Pour the reaction mixture into water, bring the reaction mixture to neutrality with 1-N hydrochloric acid, then extract the neutralized mixture with ethyl acetate. Combine the ethyl acetate extracts and evaporate to a residue comprising 0.43 g. of 6-azido-9α-fluoro-16β-methyl-1,4,6-pregnatriene-11β,17α,21-triol-3,20-dione 17,21-dipropionate. Purify by crystallization from acetone-hexane to yield 0.21 g. of purified 6-azido-9α-fluoro-16β-methyl-1,4,6-pregnatriene-11β,17α,21-triol-3,20-dione 17,21-dipropionate; $[\alpha]_D^{26°}$ + 52.9° (dimethylformamide); $\lambda_{max}^{methanol}$ 248 nm ($\epsilon$=16,900), 311 nm ($\epsilon$=7,400); m.p. = 160° (decomp).

In the above procedure, using tri-n-butylorthovalerate instead of tri-n-butylorthopropionate there is obtained 6-azido-9α-fluoro-16β-methyl-1,4,6-pregnatriene-11β,17α,21-triol-3,20-dione 17,21-orthovalerate, which, when treated with aqueous acetic acid followed by dilute sodium carbonate, yields 6-azido-9α-fluoro-16β-methyl-1,4,6-pregnatriene-11β,17α,21-triol-3,20-dione 17-monovalerate, which in turn, upon treatment with valeric anhydride in pyridine, yields 6-azido-9α-fluoro-16β-methyl-1,4,6-pregnatriene-11β,17α,21-triol-3,20-dione 17,21-divalerate.

B. Alternatively, the compound of this example is prepared from 9α-fluoro-16β-methyl-1,4-pregnadiene-11β,17α,21-triol-3,20-dione 17,21-dipropionate in the following manner:

In a manner similar to that described in Example 4, treat 9α-fluoro-16β-methyl-1,4-pregnadiene-11β,17α,21-triol-3,20-dione 17,21-dipropionate with DDQ and dry hydrogen chloride in dioxane to obtain 9α-fluoro-16β-methyl-1,4,6-pregnatriene-11β,17α,21-triol-3,20-dione 17,21-dipropionate. Treat the foregoing 1,4,6-pregnatriene with osmium tetroxide in dioxane followed by treatment of the thereby produced osmate ester with hydrogen sulfide and isolation of the resulting product to obtain 6β,7β-dihydroxy-9α-fluoro- 16β-methyl-1,4-pregnadiene-11β,17α,21-triol-3,20-dione-17,21-dipropionate; treatment thereof with methanesulfonyl chloride in pyridine yields the corresponding 6β,7β-dimethanesulfonyloxy-9α-fluoro-16β-methyl-1,4-pregnadiene-11β,17α,21-triol-3,20-dione 17,21-dipropionate. Treatment of the foregoing 6β,7β-dimethanesulfonyloxy derivative with sodium azide in dimethylformamide, according to the procedure of Example 1D, yields 6-azido-9α-fluoro-16β-methyl-1,4,6-pregnatriene-11β,17α,21-triol-3,20-dione 17,21-dipropionate. Purify by recrystallization from acetone-hexane.

EXAMPLE 6

6-Azido-9α-fluoro-16β-methyl-4,6-pregnadiene-11β,17α,21-triol-3,20-dione
(6-Azido-6-dehydrobetamethasone)

A.

6β,7β-Dihydroxy-9α-fluoro-16β-methyl-4-pregnene-11β,17α,21-triol 3,20-dione 21-acetate In a manner similar to that described in Example 1B, treat 1.5 g. of 9α-fluoro-16β-methyl-4,6-pregnadiene-11β,17α,21-triol-3,20-dione 21-acetate with 1 g. of osmium tetroxide in dioxane followed by treatment of the thereby formed osmate ester with hydrogen sulfide. Isolate and purify the resultant product in a manner similar to that described in Example 1B to obtain 0.8 g. (49% theoretical yield) of 6β,7β-dihydroxy-9α-fluoro-16β-methyl-4-pregnene-11β,17α,21-triol-3,20-dione 21-acetate. Purify by crystallization from ether-methanol, m.p. =246°–249°C $[\alpha]_D^{26°}$ +102.5 (dioxane); $\epsilon_{max}^{methanol}$ 237 nm ($\epsilon$=13,100); n.m.r. (dmso-$d_6$/$D_2O$) δ 0.92 ($C_{13}$-$CH_3$); 1.02 ($C_{16}$-$CH_3$; d,J7Hz); 1.60 ($C_{10}$-$CH_3$); 3.66 (7α-H; mult); 4.06 (11α-H; mult); 4.18 (6α-H;d,J4Hz); 5.89 ($C_4$-H).

B.

6β,7β-dimethanesulfonyloxy-9α-fluoro-16β-methyl-4-pregnene-11β,17α,21-triol-3,20-dione 21-acetate Dissolve 0.8 g. of 6β,7β-dihydroxy-9α-fluoro-16β-methyl-4-pregnene-11β,17α,21-triol-3,20-dione 21-acetate in 8 ml. of dry pyridine. Cool the solution to 0°C and add 1 ml. of methanesulfonyl chloride. Stir the reaction mixture at 0°C for 45 minutes then pour into ice water. Extract the aqueous mixture with 3 portions of methylene chloride. Wash the combined methylene chloride extracts with 3 portions of ice cold 1 normal hydrochloric acid and then with 3 portions of ice cold water. Dry the washed methylene chloride extracts over anhydrous magnesium sulfate, filter and evaporate in vacuo at room temperature to a residue comprising 6β,7β-dimethanesulfonyloxy-9α-fluoro-16β-methyl-4-pregnene-11β,17α,21-triol-3,20-dione 21-acetate (yield = 1 g.). This product was used without further purification in the step immediately following.

C.

6-Azido-9α-fluoro-16β-methyl-4,6-pregnadiene-11β,17α,21-triol-3,20-dione 21-acetate Dissolve the 6β,7β-dimethanesulfonate ester prepared as described in Example 6B in 60 ml. of a solution comprising 135 ml. of methanol, 2.25 ml. of water and 1 ml. of glacial acetic acid. Add 4 g. of sodium azide and stir the reaction mixture at room temperature in the absence of light for 19 hours. Pour the reaction mixture into ice water and extract with 4 portions of methylene chloride. Wash the combined methylene chloride extracts with 2 portions of water, then dry the methylene chloride extracts over anhydrous magnesium sulfate. Evaporate in vacuo at room temperature to a residue comprising 0.7 g. of 6-azido-9α-fluoro-16β-methyl-4,6-pregnadiene-11β,17α,21-triol-3,20-dione 21-acetate. Purify by chromatographing on a column of 100 g. of silica gel eluting with chloroform-ethyl acetate (2:1). Combine the like eluates as determined by thin layer chromatography and evaporate the combined eluates in vacuo to a residue comprising 0.373 g. (46% theoretical yield) of 6β-azido-9α-fluoro-16β-methyl-4,6-pregnadiene-11β,17α,21-triol-3,20-dione 21-acetate.

D.

6-Azido-9α-fluoro-16β-methyl-4,6-pregnadiene-11β,17α,21-triol-3,20-dione.

In a manner similar to that described in Example 1E, treat the 21-acetate ester prepared in previous Example 6C with 3.5 ml. of saturated aqueous sodium bicarbonate solution and 30 ml. of methanol. Isolate the resultant product in a manner similar to that described to obtain 0.25 g. of 6-azido-9α-fluoro-16β-methyl-4,6-pregnadiene-11β,17α,21-triol-3,20-dione. Purify by crystallization from acetone-hexane; m.p. = 170°C (decomp.) $[\alpha]_D^{26°}$ + 155.3° (dioxane); $\lambda_{max}^{methanol}$ 251 nm ($\epsilon$=14,400), 298 nm ($\epsilon$=12,700), n.m.r. (dmso-$d_6$/$D_2O$) 1.04($C_{13}$-$CH_3$); 1.09($C_{16}$-$CH_3$; D J6Hz); 1.43 ($C_{10}$-$CH_3$); 4.16 (11α-H; mult); 5.77 ($C_7$-H; D J2Hz); 5.92 ($C_4$-H).

In a manner similar to that described above, treat 9α-fluoro-16α-methyl-4,6-pregnadiene-11β,17α,21-triol-3,20-dione 21-acetate with osmium tetroxide in dioxane followed by treatment of the thereby formed 6β,7β-osmate ester with hydrogen sulfide and thence isolation of the resulting product to obtain 6β,7β-dihydroxy-9α-fluoro-16α-methyl-4-pregnene-11β,17α,21-triol-3,20-dione 21-acetate, esterifying the 6β,7β-dihydroxy compound thus prepared with methanesulfonyl chloride in pyridine to obtain 6β,7β-dimethanesulfonyloxy-9α-fluoro-16α-methyl-4-pregnene-11β,17α,21-triol-3,20-dione 21-acetate. Treatment of the foregoing 6β,7β-dimethanesulfonate ester with sodium azide in aqueous methanol-acetic acid yields 6-azido-9α-fluoro-16α-methyl-4,6-pregnadiene-11β,17α,21-triol-3,20-dione 21-acetate.

EXAMPLE 7

6-Azido-9α-fluoro-16α,17α-iso-propylidenedioxy-4,6-pregnadiene-11β, 21-diol-3,20-dione 21-acetate

A.

6β,7β-Dihydroxy-9α-fluoro-16α,17α-iso-propylidenedioxy-4-pregnene-11β,21-diol-3,20-dione 21-acetate In a manner similar to that described in Example 1B treat 9α-fluoro-16α,17α-iso-propylidenedioxy-4,6-pregnadiene-11β,21-diol-3,20-dione 21-acetate with osmium tetroxide in dioxane followed by treatment of the thereby formed 6β,7β-osmate ester with hydrogen sulfide. Isolate and purify the resultant product in a manner similar to that described in Example 1B to obtain 6β,7β-dihydroxy-9α-fluoro-16α,17α-iso-propylidenedioxy-4-pregnene-11β,21-diol-3,20-dione 21-acetate; n.m.r. ($CDCl_3$) δ 0.92 ($C_{13}$-$CH_3$); 1.67 ($C_{10}$-$CH_3$); 3.82 (7α-H; mult); 4.31 (6α-H+11α-H; mult); 4.97 (16β-H; mult); 5.90 ($C_4$-H).

B.
6β,7β-Dimethanesulfonyloxy-9α-fluoro-16α,17α-iso-propylidenedioxy-4-pregnene-11β,21-diol-3,20-dione 21-acetate In a manner similar to that described in Example 1C treat 0.72 g. of 6β,7β-dihydroxy-9α-fluoro-16β,17β-iso-propylidenedioxy-4-pregnene-11β,21-diol-3,20-dione with 1.4 ml. of methanesulfonyl chloride in 14 ml. of pyridine at 0°C. Isolate the resultant product in a manner similar to that described to obtain 0.89 g. of 6β,7β-dimethanesulfonyloxy-9α-fluoro-16α,17α-iso-propylidenedioxy-4-pregnene-11α,21-diol-3,20-dione 21-acetate which is used without further purification in the steps immediately following.

C.
6-Azido-9α-fluoro-16α,17α-iso-propylidenedioxy-4,6-pregnadiene-11α,21-diol-3,20-dione 21-acetate Treat the 6β,7β-dimethanesulfonate prepared as described in Example 7B with 5.4 g. of sodium azide in a reaction mixture comprising 135 ml. of methanol, 2.25 ml. of water and 1 ml. of acetic acid. in a manner similar to that described in Example 6C. Isolate and purify the resultant product by chromatography utilizing silica gel plates, eluting with chloroform-ethyl acetate (1:1). Combine the like eluates as determined by thin layer chromatography and evaporate in vacuo to a residue comprising 6-azido-9α-fluoro-16α,17α-iso-propylidenedioxy-4,6-pregnadiene-11β,21-diol-3,20-dione 21-acetate. Further purify by crystallization from methanol; m.p. = 185°C (decomp.); n.m.r. (CDCl$_3$) δ 0.97 ($C_{13}CH_3$); 1.47($C_{10}$-$CH_3$); 4.36 (11α-H; mult); 5.06 (16β-H; mult); 5.5 ($C_7$-H;d J2.5Hz);6.33 ($C_4$-H), $\lambda_{max}^{methanol}$ 248 nm ($\epsilon$=13,300);295 nm ($\epsilon$=9,800).

EXAMPLE 8
6-Azido-9α-fluoro-1,4,6-pregnatriene-11β,16α,17α,21-tetrol-3,20-dione 16,21-diacetate
(6-Azido-6-dehydro-triamcinolone 16,21-diacetate

A.
9α-Fluoro-1,4,6-pregnatriene-11β,16α,17α,21-tetrol-3,20-dione

In a manner similar to that described in Example 1A, to a solution of 50 g. of hydrogen chloride in 1,500 ml. of dioxane add 22.6 g. of 9α-fluoro-1,4-pregnadiene-11β,16α,17α,21-tetrol-3,20-dione 16,21-diacetate and 12.93 g. of DDQ. Stir the reaction mixture for 24 hours, then isolate and purify the resultant product in a manner similar to that described in Example 1A to give 15 g. (66% theory) of 9α-fluoro-1,4,6-pregnatriene-11β,16α,17α,21-tetrol-3,20-dione 16,21-diacetate. Purify by recrystallization from methanol-chloroform; $[\alpha]_D^{26°}$ −3.1° (dimethylformamide); $\lambda_{max}^{methanol}$ 220 nm ($\epsilon$=12,600), 250 nm ($\epsilon$=9,800) 298 nm ($\epsilon$=12,600).

B.
6β,7β-Dihydroxy-9α-fluoro-1,4-pregnadiene-11β,16α,17α,21-tetrol 3,20-dione 16,21-diacetate In a manner similar to that described in Example 1B, treat 7.5 g. of 9α-fluoro-1,4,6-pregnatriene-11β,16α,17α,21-tetrol-3,20-dione-16,21-diacetate with 4 g. of osmium tetroxide in 200 ml. of dioxane and 10 ml. of pyridine under nitrogen in the absence of light for 4 days. Treat the reaction mixture with hydrogen sulfide and isolate the resultant product in a manner similar to that described to obtain 4.7 g. (59% theory) of 6β,7β-dihydro-9α-fluoro-1,4-pregnadiene-11β,16α,17α,21-tetrol-3,20-dione 16,21-diacetate. Purify by recrystallization from ethyl acetatehexane $\lambda_{max}^{methanol}$ 240 nm ($\epsilon$=14,400), n.m.r. (dmso-d$_6$/D$_2$O) δ 0.89 ($C_{13}$-$CH_3$); 1.63 ($C_{10}$-$CH_3$); 3.70 (7α-H; mult); 4.26 (6α-H; d,J4Hz); 6.15 ($C_4$-H); 6.23 ($C_2$-H; d,d J10,2Hz); 7.27 ($C_1$-H; d,J10Hz).

C.
6β,7β-Dimethanesulfonyloxy-9α-fluoro-1,4-pregnadiene-11β,16α,17α,21-tetrol-3,20-dione 16,21-diacetate In a manner similar to that described in Example 1C treat 2.5 g. of 6β,7β-dihydroxy-9α-fluoro-1,4-pregnadiene-11β,16α,17α,21-tetrol-3,20-dione 16,21-diacetate with 5 ml. of methanesulfonylchloride in 50 ml. of pyridine at room temperature for two hours. Isolate the resultant product in a manner similar to that described to obtain 6β,7β-dimethanesulfonyloxy-9α-fluoro-1,4-pregnadiene-11β,16α,17α,21-tetrol-3,20-dione 16,21-diacetate, which is used without further purification in the step immediately following.

D.
6-Azido-9α-fluoro-1,4,6-pregnatriene-11β,16α,17α,21-tetrol-3,20-dione 16,21-diacetate In a manner similar to that described in Example 1D, treat the 6β,7β-dimethanesulfonyloxy ester prepared in Example 8C with 12.8 g. of sodium azide in 42 ml. of dimethylformamide at room temperature for 48 hours. Isolate and purify the resultant product in a manner similar to that described in Example 1D to obtain 1.29 g. (51% theory) of 6-azido-9α-fluoro-1,4,6-pregnatriene-11β,16α,17α,21-tetrol-3,20-dione 16,21-diacetate. Purify by recrystallization from acetone m.p. 160°C (decomp.) $[\alpha]_D^{26°}$ +16.4° (dimethylformamide); $\lambda_{max}^{methanol}$ 248 nm ($\epsilon$=16,000), 312 nm ($\epsilon$=7,150); $\nu_{nujol}$ 4.73 $\mu$(N$_3$)

EXAMPLE 9
6-Azido-9α-fluoro-16α-methyl-1,4,6-pregnatriene-17α,21diol-3,11 20-trione.

A. In a manner similar to that described in Example 1, treat 9α-fluoro-16α-methyl-1,4,6-pregnatriene-17α,21-diol-3,11,20-trione 21-acetate with osmium tetroxide in dioxane then with hydrogen sulfide to obtain 6β,7β-dihydroxy-9α-fluoro-16α-methyl-1,4-pregnadiene-17α,21-diol-3,11,20-trione 21-acetate. Esterify with methanesulfonyl chloride in pyridine to obtain 6β,7β-dimethanesulfonyloxy-9α-fluoro-16α-methyl-1,4-pregnadiene-17α,21-diol-3,11,20-trione 21-acetate then treat the foregoing with sodium azide in dimethylformamide to obtain 6-azido-9α-fluoro-16α-methyl-1,4,6-pregnatriene-17α,21-diol-3,11,20-trione 21-acetate. Treat the foregoing 21-acetate derivative with aqueous sodium bicarbonate in methanol according to the procedure of Example 1E to obtain 6-azido-9α-fluoro-16α-methyl-1,4,6-pregnatriene-17α,21-diol-3,11,20-trione.

B. Alternatively, the compound of this example is prepared in the following manner.

1.
6-Azido-9α-fluoro-16α-methyl-1,4,6-pregnatriene-17α,21-diol-3,11,20-trione 21-acetate To a stirred solution of 93 mg. of 6-azido-9α-fluoro-16α-methyl-1,4,6-pregnatriene-11β,17α,21-triol-3,20- dione 21-acetate in 9ml. of methylene chloride under an atmosphere of nitrogen, add 330 mg. of chromium trioxide/pyridine complex. Stir the reaction mixture under an atmosphere of nitrogen at room temperature for 1.5 hours. Filter, wash the precipitate with chloroform, combine the organic filtrates, and wash the combined filtrates with 3 portions of water. Dry over anhydrous magnesium sulfate and evaporate in vacuo at room temperature to a residue comprising 80 mg. of 6-azido-9α-fluoro-16α-methyl-1,4,6-pregnatriene-17α,21-diol-3,11,20-trione 21-acetate which is used without further purification in the step immediately following.

2.
6-Azido-9α-fluoro-16α-methyl-1,4,6-pregnatriene-17α,21-diol-3,11,20-trione Treat the 6-azido-1,4,6-pregnatriene-21-acetate derivative prepared in above Example 9B(1) with aqueous sodium bicarbonate solution in methanol in the manner described in Example 1E. Isolate and purify the resultant product in a manner similar to that described to obtain 6-azido-9α-fluoro-16α-methyl-1,4,6-pregnatriene-17α,21-diol-3,11,20-trione. Further purify by crystallization from acetone-hexane, m.p. 140°C (decomp); $[\alpha]_D^{28°}$ +148.7° (dimethylformamide); $\lambda_{max}^{methanol}$ 247 nm ($\epsilon$=14,200), 311 nm ($\epsilon$=6,400).

EXAMPLE 10
6-Azido-9α-fluoro-16β-methyl-1,4,6-pregnatriene-17α,21-diol-3,11,20-trione A. In a manner similar to that described in Example 1, treat 9α-fluoro-16β-methyl-1,4,6-pregnatriene-17α,21-diol-3,11,20-trione 21-acetate with osmium tetroxide in dioxane followed by hydrogen sulfide treatment to obtain 6β,7β-dihydroxy-9α-fluoro-16β-methyl-1,4-pregnadiene-17α,21-diol-3,11,20-trione 21-acetate. Esterify with methanesulfonyl chloride in pyridine to give 6β,7β-dimethanesulfonyloxy-9α-fluoro-16β-methyl-1,4-pregnadiene-17α,21-diol-3,11,20-trione 21-acetate, then treat the foregoing with sodium azide in dimethylformamide to obtain 6-azido-9α-fluoro-16β-methyl-1,4,6-pregnatriene-17α,21-diol-3,11,20-trione 21-acetate. Hydrolyze the foregoing 21-acetate ester with saturated aqueous sodium bicarbonate solution in methanol according to the procedure of Example 1E to obtain 6-azido-9α-fluoro-16β-methyl-1,4,6-pregnatriene-17α,21-diol-3,11,20-trione.

B. Alternatively, the compound of this example is prepared in a manner similar to that described in Example 9B by treating 6-azido-9α-fluoro-16β-methyl-1,4,6-pregnatriene-11β,17α,21-triol-3,20-dione 21-acetate with chromium trioxide pyridine complex then hydrolyzing the thereby formed 6-azido-9α-fluoro-16β-methyl-1,4,6-pregnatriene-17α,21-diol-3,11,20-trione 21-acetate with aqueous sodium bicarbonate in methanol to obtain 6-azido-9α-fluoro-16β-methyl-1,4,6-pregnatriene-17α,21-diol-3,11,20-trione. Purify by crystallization from acetone/hexane; m.p. 160°C (decomp.); $[\alpha]_D^{26°}$ +162.4° (dimethylformamide); $\lambda_{max}^{methanol}$ 247 nm ($\epsilon$=14,600), 311 nm; ($\epsilon$=6,500).

EXAMPLE 11
6-Azido-9α-fluoro-16β-methyl-4,6-pregnadiene-17α,21-diol-3,11,20-trione A. In a manner similar to that described in Example 1B and 1C, treat 9α-fluoro-16β-methyl-4,6-pregnadiene-17α,21-diol-3,11,20-trione 21-acetate with osmium tetroxide in dioxane followed by hydrogen sulfide treatment to obtain 6β,7β-dihydroxy-9α-fluoro-16β-methyl-4-pregnene-17α,21-diol-3,11,20-trione 21-acetate followed by esterification with methanesulfonyl chloride in pyridine to obtain 6β,7β-dimethanesulfonyloxy-9α-fluoro-16β-methyl-4-pregnene-17α,21-diol-3,11,20-trione 21-acetate. Treat the foregoing with sodium azide in aqueous methanolic acetic acid according to the procedure of Example 6C to obtain 6-azido-9α-fluoro-16β-methyl-4,6-pregnadiene-17α,21-diol-3,11,20-trione 21-acetate. Hydrolysis thereof with sodium bicarbonate in aqueous methanol according to the procedure of Example 1E yields 6-azido-9α-fluoro-16β-methyl-4,6-pregnadiene-17α,21-diol-3,11,20-trione.

B. Alternatively, the compound of this example is prepared in a manner similar to that described in Example 9B as follows. Oxidize 0.37 g. of 6-azido-9α-fluoro-16β-methyl-4,6-pregnadiene-11β,17α,21-triol-3,20-dione 21-acetate with 1.2 g. of chromium trioxide-pyridine complex in 37 ml. of methylene chloride. Isolate and purify the resultant product in a manner similar to that described in Example 9B(1) to obtain 6-azido-9α-fluoro-16β-methyl-4,6-pregnadiene-17α,21-diol-3,11,20-trione 21-acetate. Hydrolyze the foregoing 21-acetate in 90 ml. of methanol with 10 ml. of saturated aqueous sodium bicarbonate in a manner similar to that described in Example 9B(2) to obtain 191 mg. (57% theoretical yield) of 6-azido-9α-fluoro-16β-methyl-4,6-pregnadiene-17α,21-diol-3,11,20-trione. Purify by recrystallization from acetonehexane; m.p. 135°–140°C (decomp.); $[\alpha]_D^{26°}$ +180.6° (dimethylformamide); $\lambda_{max}^{methanol}$ 249 nm;($\epsilon$ = 13,300), 295 nm; ($\epsilon$ = 10,700).

EXAMPLE 12
Preparation of 6-Azido-9α-fluoro-16α-methyl-1,4,6-pregnatriene-11β,17α,21-triol-3,20-dione 21-acetate Utilizing tetra-n-Butylammonium Azide as Reagent To a solution containing 0.4 g. of tetra-n-butylammonium azide in 10 ml. of chloroform add 100 mg. of 6β,7β-dimethanesulfonyloxy-9α-fluoro-16α-methyl-1,4-pregnadiene-11β,17α,21-triol-3,20-dione 21-acetate and stir the reaction mixture at room temperature under an atmosphere of nitrogen in the absence of light for five days. Add 300 ml. of ethyl acetate, wash with three 100 ml. portions of water, dry over sodium sulfate and evaporate in vacuo to a residue comprising 6-azido-9α-fluoro-16α-methyl-1,4,6-pregnatriene-11β,17α,21-triol-3,20-dione 21-acetate (yield, 80 mg.). Purify by thin layer chromatography, developing with chloroform-ethyl acetate (2:1). Combine the like fractions, elute with ethyl acetate, and evaporate the eluates in vacuo to a residue comprising 6-azido-9α-fluoro-16α-methyl-1,4,6-pregnatriene-11β,17α,21-triol-3,20-dione 21-acetate (yield, 12.4 mg., 16% theory) which was identical with the compound prepared as described in Example 1D.

Similarly, tetra-methylguanidinium azide may be used instead of the tetra-n-butylammonium azide in the above procedure to obtain the compound of this example.

EXAMPLE 13

6-Azido-1,4,6-pregnatriene-11$\beta$,17$\alpha$,21-triol-3,20-dione (6-Azido-6-dehydroprednisolone)

A.

6$\beta$,7$\beta$-Dihydroxy-1,4-pregnadiene-11$\beta$,17$\alpha$,21-triol-3,20-dione 21-acetate In a manner similar to that described in Example 1B, treat 4.7 g. of 1,4,6-pregnatriene-11$\beta$,17$\alpha$,21-triol-3,20-dione 21-acetate with 3 g. of osmium tetroxide in 225 ml. of dioxane and 11.25 ml. of pyridine at room temperature for five days. Isolate the resultant product in a manner similar to that described in Example 1B to obtain a residue comprising 3.95 g. 6$\beta$,7$\beta$-dihydroxy-1,4-pregnadiene-11$\beta$,17$\alpha$,21-triol-3,20-dione 21-acetate. Purify by trituration with chloroform then methanol, filter the resultant solid to obtain 6$\beta$,7$\beta$-dihydroxy-1,4-pregnadiene-11$\beta$,17$\alpha$,21-triol, 3,20-dione 21-acetate, which can be used without further purification in the procedure of Example 13B. If desired, further purify via thin layer chromatography developing with methanol-chloroform-ethyl acetate (1:4:4); combine like fractions, elute with ethyl acetate, evaporate the eluate to a residue, recrystallize the residue from methanol to obtain 6$\beta$,7$\beta$-dihydroxy-1,4-pregnadiene-11$\beta$,17$\alpha$,21-triol-3,20-dione 21-acetate; m.p. 240°–250°C; $\lambda max^{methanol}$ 245 nm ($\epsilon$ =13,400) n.m.r. (dmso-d$_6$/D$_2$O) $\delta$ 0.80 (C$_{13}$-CH$_3$); 1.53 (C$_{10}$-CH$_3$); 3.13 (7$\alpha$-H; d,d J10,5Hz); 4.20 (6$\alpha$-H; d,J3Hz); 6.03 (C$_4$-H); 6.12 (C$_2$-H; d,d J10,2Hz); 7.30 (C$_1$-H; d J,10Hz).

B.

6$\beta$,7$\beta$-Dimethanesulfonyloxy-1,4-pregnadiene-11$\beta$,17$\alpha$,21-triol-3,20-dione 21-acetate In a manner similar to that described in Example 1C, treat 1.32 g. of 6$\beta$,7$\beta$-dihydroxy-1,4-pregnadiene-11$\beta$,17$\alpha$,21-triol-3,20-dione 21-acetate in 26.4 ml. of pyridine with 2.64 ml. of methanesulfonyl chloride at room temperature for 1.5 hours. Pour the reaction mixture into water and extract the aqueous mixture with ethyl acetate and evaporate the ethyl acetate extracts in vacuo to a residue comprising 6$\beta$,7$\beta$-dimethanesulfonyloxy-1,4-pregnadiene-11$\beta$,17$\alpha$,21-triol-3,20-dione 21-acetate (yield, 1.95 g.) which is used without further purification in the following reaction.

C.

6-Azido-1,4,6-pregnatriene-11$\beta$,17$\alpha$,21-triol-3,20-dione 21-acetate

To the 6$\beta$,7$\beta$-dimethanesulfonyloxy-1,4-pregnadiene-11$\beta$,17$\alpha$,21-triol-3,20-dione 21-acetate prepared in above Example 13B in 25 ml. of dimethylformamide under an atmosphere of nitrogen at room temperature, add 4.87 g. of sodium azide. Stir the reaction mixture at room temperature in the dark for 18 hours, then isolate the resultant product in a manner similar to that described in Example 1D to obtain 1.6 g. of a product comprising 6-azido-1,4,6-pregnatriene-11$\beta$,17$\alpha$,21-triol-3,20-dione 21-acetate. Purify by chromatography on a column of 160 g. of silica gel, eluting with chloroform-ethyl acetate (1:1) to obtain 0.41 g. of 6-azido-1,4,6-pregnatriene-11$\beta$,17$\alpha$,21-triol-3,20-dione 21-acetate.

D

6-Azido-1,4,6-pregnatriene-11$\beta$,17$\alpha$,21-triol-3,20-dione

Hydrolyze the 21-acetate product of Example 13C in 56 ml. of methanol and 6.2 ml. of saturated aqueous sodium bicarbonate for two hours at room temperature. Isolate the resultant product in a manner similar to that described in Example 1E to obtain 6-azido-1,4,6-pregnatriene-11$\beta$,17$\alpha$,21-triol-3,20-dione (yield, 0.22 g.; 72% theory). Purify by recrystallization from acetone-hexane m.p. 150°C (decomp.) $[\alpha]_D^{26°}$ + 41.3° (dimethylformamide); $\lambda max^{methanol}$ 250 nm ($\epsilon$ =15,800), 310 nm ($\epsilon$ =7,700)

EXAMPLE 14

6-Azido-1,4,6-pregnatriene-17$\alpha$,21-diol-3,11,20-trione (6-Azido 6-dehydroprednisone)

A.

6$\beta$,7$\beta$-Dihydroxy-1,4-pregnadiene-17$\alpha$,21-diol-3,11,20-trione 21-acetate In a manner similar to that described in Example 1B, treat 3.13 g. of 1,4,6-pregnatriene-17$\alpha$,21-diol-3,11,20-trione 21-acetate with 2 g. of osmium tetroxide in 150 ml. of dioxane and 7.5 ml. of pyridine at room temperature for four days. Isolate the resultant product in a manner similar to that described and purify the resultant product by thin layer chromatography, developing with methanol-ethyl acetate-chloroform (2:25:25). Combine like fractions, elute with ethyl acetate, evaporate the eluate in vacuo, recrystallize the resultant residue from methanol to obtain 6$\beta$,7$\beta$-dihydroxy-1,4-pregnadiene-17$\alpha$,21-diol-3,11,20-trione 21-acetate (yield, 550 mg. 18.5% theory); m.p. 290°–292°C $[\alpha]_D^{26°}$ + 67° (pyridine); $\lambda max^{methanol}$ 238 nm ($\epsilon$ =12,600) n.m.r. (dmso d$_6$/D$_2$O) $\delta$0.60 (C$_{13}$-CH$_3$); 1.52 (C$_{10}$-CH$_3$); 3.30 (7$\alpha$-H; mult); 4.21 (6$\alpha$-H; d,J3Hz); 6.11 (C$_4$-H); 6.08 (C$_2$-H; d,dJ10,2.5Hz); 6.76 (C$_1$-H; d,J10Hz).

B. 6$\beta$,7$\beta$-Dimethanesulfonyloxy-1,4-pregnadiene-17$\alpha$,21-diol-3,11,20-trione 21-acetate In a manner similar to that described in Example 1C, treat the 6$\beta$,7$\beta$-dihydroxy-1,4-pregnadiene-17$\alpha$,21-diol-3,11,20-trione 21-acetate prepared in Example 14A with methanesulfonyl chloride in pyridine. Isolate the resultant product in a manner similar to that described in Example 1C to obtain 6$\beta$,7$\beta$-dimethanesulfonyloxy-1,4-pregnadiene-17$\alpha$,21-diol-3,11,20-trione 21-acetate which is used without further purification in the procedure of Example 14C immediately following.

C.

6-Azido-1,4,6-pregnatriene-17$\alpha$,21-diol-3,11,20-trione 21-acetate

In a manner similar to that described in Example 1D treat the 6$\beta$,7$\beta$-dimethanesulfonyloxy-1,4-pregnadiene intermediate prepared in Example 14B with sodium azide in dimethylformamide. Isolate and purify the resultant product in a manner similar to that described to obtain 6-azido-1,4,6-pregnatriene-17,21-diol-3,11,20-trione 21acetate.

D.

6-Azido-1,4,6-pregnatriene-17α,21-diol-3,11,20-trione

In a manner similar to that described in Example 1E treat the 6-azido-1,4,6-pregnatriene-17α,21-diol-3,11,20-trione 21-acetate prepared in Example 14C with aqueous sodium bicarbonate in methanol. Isolate and purify the resultant product in a manner similar to that described to obtain 6-azido-1,4,6-pregnatriene-17α,21-diol-3,11,20-trione.

EXAMPLE 15

6-Azido-4,6-pregnadiene-17α,21-diol-3,11,20-trione 21-acetate (6-Azido-6-dehydrocortisone 21-acetate)

A.

6β,7β-Dihydroxy-4-pregnene-17α,21-diol-3,11,20-trione 21-acetate

In a manner similar to that described in Example 1B, treat 0.5 g. of 4,6-pregnadiene-17α,21-diol-3,11,20-trione 21-acetate with 0.4 g. of osmium tetroxide in 11 ml. of dioxane and 0.5 ml. of pyridine at room temperature in the dark under an atmosphere of nitrogen for 3.5 days. Isolate in a manner similar to that described and purify by chromatographing on silica gel plates developing with ethyl acetate-chloroform-methanol (4.5:4.5:1). Combine like fractions, elute with ethyl acetate, and evaporate the eluate to a residue comprising 6β,7β-dihydroxy-4-pregnene-17α,21-diol-3,11,20-trione 21-acetate (yield = 0.123 g., 23% theory). Further purify by recrystallization from methanol-ethyl acetate; m.p. = 240°–243°C; $[\alpha]_D^{26°}$ + 122° (pyridine); λ max$^{methanol}$ 230 nm (ε =11,700); n.m.r. (dmso-d$_6$/D$_2$O) δ 0.48(C$_{13}$-CH$_3$); 1.50 (C$_{10}$-CH$_3$); 3.46 (7α-H; mult); 4.04 (6α-H; d J2Hz); 5.75 (C$_4$-H).

A second series of like eluates, when combined and evaporated to a residue, yields 6α,7α-dihydroxy-4-pregnene-17α,21-diol-3,11,20-trione 21-acetate (yield = 0.068 g; 13% theory) which, when further purified by recrystallization from methanolethyl acetate has a m.p. of 277°–281°C; $[\alpha]_D^{26°}$ + 144.4° (pyridine); λ max$^{methanol}$ 240 nm (ε =13,400) n.m.r. (dmso-d$_6$/D$_2$O) δ 0.50 (C$_{13}$-CH$_3$); 1.35 (C$_{10}$-CH$_3$); 3.80 (7β-H; mult); 4.20 (6β-H; mult); 6.03 (C$_4$-H; d J2Hz).

B.

6β,7β-Dimethanesulfonyloxy-4-pregnene-17α,21-diol-3,11,20-trione 21-acetate

In a manner similar to that described in Example 1C, treat 6β,7β-dihydroxy-4-pregnene-17α,21-diol-3,11,20-trione 21-acetate with methanesulfonyl chloride in pyridine. Isolate the resultant product in a manner similar to that described to obtain 6β,7β-dimethanesulfonyloxy-4-pregnene-17α,21-diol-3,11,20-trione 21-acetate which is used without further purification in the reaction immediately following.

C.

6-Azido-4,6-pregnadiene-17α,21-diol-3,11,20-trione 21-acetate

In a manner similar to that described in Example 6C, treat 6β,7β-dimethanesulfonyloxy-4-pregnene-17α,21-diol-3,11,20-trione 21-acetate with sodium azide in aqueous methanol in the presence of acetic acid. Isolate and purify the resultant product in a manner similar to that described to obtain 6-azido-4,6-pregnadiene-17α,21-diol-3,11,20-trione 21-acetate. D. Treatment of 6α,7α-dihydroxy-4-pregnene-17α,21-diol-3,11,20-trione 21-acetate with methanesulfonyl chloride in pyridine in a manner similar to that described in Example 1C yields 6α,7α-dimethanesulfonyloxy-4-pregnene-17α,21-diol-3,11,20-trione 21-acetate, which when isolated in a manner similar to that described in Example 1C and immediately treated with sodium azide in aqueous methanol in the presence of acetic acid in a manner similar to that described in Example 6C, yields a product devoid of 6-azido-4,6-pregnadiene-17α,21-diol-3,11,20-trione 21-acetate.

EXAMPLE 16

6-Azido-9α-fluoro-4,6-pregnadiene-17α,21-diol-3,11,20-trione 21-acetate

A.

6β,7β-Dihydroxy-9α-fluoro-4-pregnene-17α,21-diol-3,11,20-trione 21-acetate

In a manner similar to that described in Example 1B, treat 150 mg. of 9α-fluoro-4,6-pregnadiene-17α,21-diol-3,11,20-trione 21-acetate with 94 mg. of osmium tetroxide in 2.85 ml. of dioxane and 0.15 ml. of pyridine at room temperature in the dark for 3.5 days. Isolate in a manner similar to that described and purify by chromatographing on preparative thin layer plates developing with ethyl acetate-chloroform (1:1). Combine like fractions, elute with ethyl acetate and evaporate the eluates to a residue comprising 6β,7β-dihydroxy-9α-fluoro-4-pregnene-17α,21-diol-3,11,20-trione 21-acetate. Yield = 100 mg., (61% theory). Further purify by recrystallization from methanol m.p. 255°–260°C; $[\alpha]_D^{26°}$ + 72.8° (pyridine) λ max$^{methanol}$ 228 nm (ε = 13,200) n.m.r. (dmso-d$_6$/D$_2$O) δ 0.52 (C$_{13}$-CH$_3$); 1.58 (C$_{10}$-CH$_3$); 3.70(7α-H-mult); 4.12 (6α-H; d,J 3.5 Hz); 5.86 (C$_4$-H).

B. Treat 6β,7β-dihydroxy-9α-fluoro-4-pregnene-17α,21-diol-3,11,20-trione 21-acetate with methanesulfonyl chloride in pyridine according to the procedure of Example 1C to obtain 6β,7β-dimethanesulfonyloxy-9α-fluoro-4-pregnene-17α,21-diol-3,11,20-trione 21-acetate; then treat the thus obtained 6β,7β-dimethanesulfonyloxy ester intermediate with sodium azide in aqueous methanol in the presence of acetic acid according to the procedure of Example 6C to obtain 6-azido-9α-fluoro-4,6-pregnadiene-17α,21-diol-3,11,20-trione 21-acetate.

EXAMPLE 17

6-Azido-9α-fluoro-4,6-pregnadiene-11β,17α,21-triol-3,20-dione 21-acetate
(6-Azido-9α-fluoro-6-dehydro-hydrocortisone 21-acetate

A.

6β,7β-Dihydroxy-9α-fluoro-4-pregnene-11β,17α,21-triol 3,20-dione 21-acetate

In a manner similar to that described in Example 1B, treat 125 mg. of 9α-fluoro-4,6-pregnadiene-11β,17α,21-triol-3,20-dione 21-acetate with 94 mg. of osmium tetroxide in 2.85 ml. of dioxane and 0.15 ml. of pyridine under an atmosphere of nitrogen at room temperature in the absence of light for 3.5 days. Isolate the resultant product in a manner similar to that described in Example 1B and purify by chromatographing on preparative thin layer plates developing with ethyl acetate-chloroform-methanol (4.5:4.5:1). Combine like eluates, elute with ethyl acetate and evaporate the eluate to a residue comprising 6β,7β-dihydroxy-9α- fluoro-4-pregnene-11β,17α,21-triol-3,20-dione 21-acetate (yield, 95 mg., 70% theory). Further purify by recrystallization from acetone-ether m.p. 248°–250°C; $[\alpha]_D^{26°}$ +69° (pyridine); λ max$^{methanol}$ 237 nm (ε =12,500) n.m.r. (dmso d$_6$/D$_2$O)δ 0.78 (C$_{13}$-CH$_3$); 1.60 (C$_{10}$-CH$_3$); 3.65 (7α-H; d,d J5.5, 3.5 Hz); 4.13 (11α-H; mult); 4.18 (6α-H; d,J3.5 Hz); 5.88 (C$_4$-H).

B. Treat 6β,7β-dihydroxy-9α-fluoro-4-pregnene-11β,17α,21-triol-3,20-dione 21-acetate with methanesulfonyl chloride in pyridine according to the procedure of Example 1C to obtain 6β,7β-dimethanesulfonyloxy-9α-fluoro-4-pregnene-11β,17α,21-triol-3,20-dione 21-acetate; then treat the thus obtained 6β,7β-dimethanesulfonyloxy ester intermediate with sodium azide in aqueous methanol in the presence of acetic acid according to the procedure of Example 6C to obtain 6-azido-9α-fluoro-4,6-pregnadiene-11β,17α,21-triol-3,20-dione 21-acetate.

EXAMPLE 18

Other 6-Azido-4,6-pregnadiene-21-ol-3,20-dione 21-lower alkanoates

A. 6β,7β-dihydroxy-4-pregnene-21-ol-3,20-dione 21-lower alkanoates

1. In a manner similar to that described in Example 1B, treat 1.1 g. of 9α,11β-dichloro-16α-methyl-1,4,6-pregnatriene-17α,21-diol-3,20-dione 17,21-butyrate with 0.5 g. of osmium tetroxide in 10 ml. of dioxane and 0.5 ml of pyridine under an atmosphere of nitrogen in the dark at room temperature for four days. Isolate the resultant product in a manner similar to that described, then purify by chromatographing on silica gel, eluting first with chloroform then with ethyl acetate-chloroform (1:1). Combine the like ethyl acetate-chloroform eluates as determined by thin layer chromatography and evaporate the combined eluates to a residue comprising 6β,7β-dihydroxy-9α,11β-dichloro-16α-methyl-1,4-pregnadiene-17α,21-diol-3,20-dione 17,21-dibutyrate (yield, 0.43 g.). Further purify by crystallization from acetone-hexane to obtain purified 6β,7β-dihydroxy-9α,11β-dichloro-16α-methyl-1,4-pregnadiene-17α,21-diol-3,20-dione 17,21-dibutyrate (yield = 380 mg.); n.m.r. (CDCl$_3$)δ1.20 (C$_{13}$-CH$_3$); 1.88 (C$_{10}$-CH$_3$); 3.94 (7α-H; d,d J8,4 Hz); 4.46 (6α-H; d, J4.5 Hz); 4.70 (11α-H; mult); 6.26 (C$_4$-H); 6.35 (C$_2$-H; d,d J11,2Hz); 7.18 (C$_1$-H; d,J11 Hz).

Further purify the filtrates of the above recrystallization via thin layer chromatography to obtain 6α,7α-dihydroxy-9α,11β-dichloro-16α-methyl-1,4-pregnadiene-17α,21-diol-3,20-dione 17,21-dibutyrate (yield, 13 mg.) n.m.r. (CDCl$_3$)δ 1.18 (C$_{13}$-CH$_3$); 1.90 (C$_{10}$-CH$_3$); 4.5 (11α-H + 7β-H; mult); 4.81 (6β-H + 21-CH$_2$); 6.17 (C$_4$-H; d,J 2Hz); 6.34 (C$_2$-H; d,d J10, 2Hz); 7.16 (C$_1$-H; d, J10 Hz).

2. In a manner similar to that described in Example 1B and above Example 18A(1), treat each of the following 4,6-pregnadienes with osmium tetroxide in dioxane and pyridine under nitrogen at room temperature in the absence of light:

1. 9α-fluoro-16β-methyl-16α,17α-oxido-1,4,6-pregnatriene-11β,21-diol-3,20-dione 21-acetate;
2. 9α-chloro-16α-methyl-1,4,6-pregnatriene-11β,17α,21-triol-3,20-dione 21-acetate;
3. 9α-chloro-16β-methyl-1,4,6-pregnatriene-11β,17α,21-triol-3,20-dione 21-acetate;
4. 9α-chloro-16α-methyl-4,6-pregnadiene-11β,17α,21-triol-3,20-dione 21-acetate;
5. 9α-chloro-16β-methyl-4,6-pregnadiene-11β,17α,21-triol-3,20-dione 21-acetate;
6. 9α-bromo-16α-methyl-1,4,6-pregnatriene-11β,17α,21-triol-3,20-dione 21-acetate;
7. 9α-bromo-16β-methyl-1,4,6-pregnatriene-11β,17α,21-triol-3,20-dione 21-acetate;
8. 9α-bromo-16α-methyl-4,6-pregnadiene-11β,17α,21-triol-3,20-dione 21-acetate;
9. 9α-bromo-16β-methyl-4,6-pregnadiene-11β,17α,21-triol-3,20-dione 21-acetate;
10. 16α-ethyl-4,6-pregnadiene-11β,17α,21-triol-3,20-dione 21-acetate;
11. 4,6-pregnadiene-21-ol-3,20-dione 21 acetate;
12. 16α-n-butyl-4,6-pregnadiene-17α,21-diol-3,11,20-trione 21-acetate;
13. 9α-chloro-11β-fluoro-16β-methyl-1,4,6-pregnatriene-17α,21-diol-3,20-dione 21-acetate;
14. 9α-bromo-11β-chloro-16β-methyl-1,4,6-pregnatriene-17α,21-diol-3,20-dione 21-acetate;
15. 9α,11β-dichloro-16α,17α-isopropylidenedioxy-1,4,6-pregnatriene-21-ol-3,20-dione 21-acetate;
16. 9α,11β-dichloro-1,4,6-pregnatriene-17α,21-diol-3,20-dione 21-acetate.

Isolate and purify each of the resultant products in a manner similar to that described in Example 1B to obtain respectively:

1. 6β,7β-dihydroxy-9α-fluoro-16β-methyl-16α,17α-oxido-1,4-pregnadiene-11β,21-diol-3,20-dione 21-acetate;
2. 6β,7β-dihydroxy-9α-chloro-16α-methyl-1,4-pregnadiene-11β,17α, 21-triol-3,20-dione 21-acetate;
3. 6β,7β-dihydroxy-9α-chloro-16β-methyl-1,4-pregnadiene -11β,17α, 21-triol-3,20-dione 21-acetate;
4. 6β,7β-dihydroxy-9α-chloro-16α-methyl-4-pregnene-11β,17α, 21-triol-3,20-dione 21-acetate;
5. 6β,7α-dihydroxy-9α-chloro-16β-methyl-4-pregnene-11β,17α,21-triol-3,20-dione 21-acetate;
6. 6β,7β-dihydroxy-9α-bromo-16α-methyl-1,4-pregnadiene-11β,17α, 21-triol-3,20-dione 21-acetate;
7. 6β,7β-dihydroxy-9α-bromo-16β-methyl-1,4-pregnadiene-11β,17α,21-triol-3,20-dione 21-acetate;
8. 6β,7β-dihydroxy-9α-bromo-16α-methyl-4-pregnene-11β,17α, 21-triol-3,20-dione 21-acetate;
9. 6β,7β-dihydroxy-9α-bromo-16β-methyl-4-pregnene-11β, 17α, 21-triol-3,20-dione 21-acetate;
10. 6β, 7β-dihydroxy-16α-ethyl-4-pregnene-11β, 17α, 21-triol-3,20-dione 21-acetate;
11. 6β, 7β-dihydroxy-4-pregnene-21, 01-3,20-dione 21-acetate;
12. 6β, 7β-dihydroxy-16α-n-butyl-4-pregnene-17α, 21-diol-3, 11, 20-trione 21-acetate;
13. 6β,7β-dihydroxy-9α-chloro-11β-fluoro-16β-methyl-1,4-pregnadiene-17α,21-diol-3,20-dione 21-acetate;
14. 6β,7β-dihydroxy-9α-bromo-11β-chloro-16β-methyl-1,4-pregnadiene-17α,21-diol-3,20-dione 21-acetate;
15. 6β,7β-dihydroxy-9α,11β-dichloro-16α, 17α-isopropylidenedioxy-1,4-pregnadiene-21-ol-3,20-dione 21-acetate;
16. 6β,7β-dihydroxy-9α,11β-dichloro-1,4-pregnadiene-17α,21-diol-3,20-dione 21-acetate.

B.
6β,7β-Dimethanesulfonyloxy-4-pregnene-21-ol-3,20-dione 21-lower alkanoates 1. In a manner similar to that described in Example 1C, treat the 6β, 7β-dihydroxy-4-pregnenes prepared in above Example 18A(1) with methanesulfonylchloride in pyridine to obtain 6β,7β-dimethanesulfonyloxy-9α,11β-dichloro-16α-methyl-1,4-pregnadiene-17α,21-diol3,20-dione 17,21dibutyrate. 2. In a similar fashion, treat each of the 6β, 7β-dihydroxy-4-pregnenes in above Example 18A(2) with methanesulfonyl chloride in pyridine. Isolate and purify each of the resultant products in a manner similar to that described to obtain respectively:

1. 6β,7β-dimethanesulfonyloxy-9α-fluoro-16β-methyl-16α,17α-oxido-1,4-pregnadiene-11α,21-diol-3,20-dione 21-acetate;
2. 6β,7β-dimethanesulfonyloxy-9α-chloro-16α-methyl-1,4-pregnadiene-11β,17α-21-triol-3,20-dione 21-acetate;
3. 6β,7β-dimethanesulfonyloxy-9α-chloro-16β-methyl-1,4-pregnadiene-11β, 17α21-triol-3,20-dione 21-acetate;
4. 6β,7β-dimethanesulfonyloxy-9α-chloro-16α-methyl-4-pregnene-11β,17α,21-triol-3,20-dione 21-acetate;
5. 6β,7β-dimethanesulfonyloxy-9α-chloro-16β-methyl-4-pregnene-11β,17α,21-triol-3,20-dione 21-acetate;
6. 6β,7β-dimethanesulfonyloxy-9α-bromo-16α methyl-1,4-pregnadiene-11β, 17α, 21-triol-3,20-dione 21-acetate;
7. 6β,7β-dimethanesulfonyloxy-9α-bromo-16β-methyl-1,4-pregnadiene-11β,17α,21-triol-3,20-dione 21-acetate;
8. 6β,7β-dimethanesulfonyloxy-9α-bromo-16α-methyl-4-pregnene-11β, 17α21-triol-3,20-dione 21-acetate;
9. 6β,7β-dimethanesulfonyloxy-9α-bromo-16β methyl-4-pregnene-11β,17α,21-triol-3,20-dione 21-acetate;
10. 6β,7β-dimethanesulfonyloxy-16α-ethyl-4-pregnene-11β,17α,21-triol-3,20-dione 21-acetate;
11. 60β,7β-dimethanesulfonyloxy-4-pregnene-21-ol-3,20-dione 21-acetate
12. 6β,7β-dimethanesulfonyloxy-16α-n-butyl-4-pregnene-17α,21-diol-3,11,20-trione 21-acetate;
13. 6β, 7β-dimethanesulfonyloxy-9α-chloro-11β-fluoro-16β-methyl-1,4-pregnadiene-17α,21-diol-3,20-dione 21-acetate;
14. 6β,7β-dimethanesulfonyloxy-9α-bromo-11β-chloro-16β-methyl-1,4-pregnadiene-17α,21-diol-3,20-dione 21-acetate;
15. 6β,7β-dimethanesulfonyloxy-9α,11β-dichloro-16α,17α-iso-propylidenedioxy-1,4-pregnadiene-21-ol-3,20-dione 21-acetate;

C. 6-Azido-4,6-pregnadiene-21-ol-3,20-dione 21-lower alkanoates

1. In a manner similar to that described in Example 1D, 6C and in Example 12, treat 6β, 7β-dimethanesulfonyloxy-9α,11β-dichloro-16α-methyl-1,4-pregnadiene-17α,21-diol-3,20-dione 17,21 -dibutyrate with an azide salt in a non-reactive solvent. Isolate and purify the resultant product in a manner similar to that described in Example 1D to obtain 6azido-9α,11β-dichloro-16α-methyl-1,4-pregnadiene-17α,21-diol-3,20-dione 17,21-dibutyrate.

2. In a manner similar to that described in Examples 1D, 6C and in Example 12, treat each of the 6β,7β-dimethanesulfonyloxy intermediates prepared in Example 18β(2) with an azide salt in a nonreactive solvent. Isolate and purify each of the resultant products in a manner similar to that described in Example 1D, 6C and Example 12 to obtain respectively:

1. 6-azido-9α-fluoro-16β-methyl-16α, 17α-oxido-1,4,6-pregnatriene-11β,21-diol-3,20-dione 21-acetate,
2. 6-azido-9α-chloro-16α-methyl-1,4,6-pregnatriene-11β,17α, 21-triol-3,20-dione 21-acetate,
3. 6-azido-9α-chloro-16β-methyl-1,4,6-pregnatriene-11β,17α, 21-triol-3,20-dione 21-acetate,
4. 6-azido-9α-chloro-16α-methyl-4,6-pregnadiene-11β,17α, 21-triol-3,20-dione 21-acetate,
5. 6-azido-9α-chloro-16β-methyl-4,6-pregnadiene-11β,17α, 21-triol-3,20-dione 21-acetate,
6. 6-azido-9α-bromo-16α-methyl-1,4,6-pregnatriene-11β,17α,21-triol-3,20-dione 21-acetate, 7. 6-azido-9α-bromo-16β-methyl-1,4,6-pregnatriene-11β,17α,21-triol-3,20-dione 21-acetate,
8. 6-azido-9α-bromo-16α-methyl-4,6-pregnadiene-11β,17α,21-triol-3,20-dione 21-acetate,
9. 6-azido-9α-bromo-16β-methyl-4,6-pregnadiene-11β,17α,21-triol-3,20-dione 21-acetate,
10. 6-azido-16α-ethyl-4,6-pregnadiene-11β, 17α, 21-triol-3,20-dione 21-acetate,
11. 6-azido-4,6-pregnadiene-21-ol-3,20-dione 21-acetate,
12. 6-azido-16α-n-butyl-4,6-pregnadiene-17α, 21-diol-3,11,20-trione 21-acetate,
13. 6-azido-9α-chloro-11β-fluoro-16β-methyl-1,4,6-pregnatriene-17α,21-diol-3,20-dione 21-acetate,
14. 6-azido-9α-bromo-11β-chloro-16β-methyl-1,4,6-pregnatriene-17α, 21-diol-3,20-dione 21-acetate,
15. 6-azido-9α,11β-dichloro-16α,17α-isopropylidenedioxy-1,4,6-pregnatriene-21-ol-3,20-dione 21-acetate,
16. 6-azido-9α,11α-dichloro-1,4,6-pregnatriene-17α, 21-diol-3,20-dione 21-acetate.

EXAMPLE 19
6-Azido-9α-fluoro-11-oxygenated-16-methyl-17α-hydroxy-1,4,6-pregnatriene-3,20-diones

A.
6β,7β-Dihydroxy-9α-fluoro-11-oxygenated-17α-hydroxy-1,4-pregnadiene-3,20-diones 1. In a manner similar to that described in Example 1B, treat 1.84 g. of 9α-fluoro-16α-methyl-1,4,6-pregnatriene-11β,17α-diol-3,20-dione with 1.25 g. of osmium tetroxide in 50 ml. of dioxane and 15 ml. of pyridine at room temperature under an atmosphere of nitrogen in the absence of light for 2.5 days. Isolate the resultant product in a manner similar to that described in Example 1B to obtain 6β,7β-dihydroxy-9α-fluoro-16α-methyl-1,4-pregnadiene-11β,17α-dioc-3,20-dione (yield= 0.83 g., 42% theory). 2. In similar manner, treat each of the following with osmium tetroxide in pyridine-dioxane: 9α-fluoro-16β-methyl-1,4,6-pregnatriene-11β,17α-diol-3,20-dione; 9α-fluoro-16α-methyl-1,4,6-pregnatriene-17α-ol-3,11,20-trione and 9α-fluoro-16β-methyl-1,4,6-pregnatriene-17α-ol-3,11,20-trione. Isolate and purify each of the resultant respective products in a manner similar to that described in Example 1B to obtain 6β,7β-dihydroxy-9α-fluoro-16β- methyl-1,4-pregnadiene-11β,17α-diol-3,20-dione; 6β,7β-dihydroxy-9α-fluoro-16α-methyl-1,4-pregnadiene-17α-ol-3,11,20-trione and 6β,7β -dihydroxy-9α-fluoro-16β-methyl-1,4-pregnadiene-17α-ol-3,11,20-trione.

B. 6β,7β-Dimethanesulfonyloxy-9α-fluoro-11-oxygenated-16-methyl-1,4-pregnadiene-17α-ol-3,20-diones In a manner similar to that described in Example 1C, treat 0.83 g. of 6β,7β-dihydroxy-9α-fluoro-16α-methyl-1,4-pregnadiene-11β,17α-diol-3,20-dione in 17ml. of pyridine with 1.67 ml. of methanesulfonyl chloride at room temperature for two hours. Isolate the resultant product in a manner similar to that described to obtain 1.2 g. of 6β,7β-dimethanesulfonyloxy-9α-fluoro-16α-methyl-1,4-pregnadiene-11β,17α-diol-3,20-dione which is used without further purification in Procedure 19C immediately following.

In a manner similar to that described in Example 1C, treat each of the 6β,7β-dihydroxy-1,4-pregnadienes prepared in Example 19A(2) with methanesulfonyl chloride in pyridine. Isolate and purify each of the resultant products in a manner described to obtain respectively: 6β,7β-dimethanesulfonyloxy-9α-fluoro-16β-methyl-1,4-pregnadiene-11β,17α-diol-3,20-dione; 6β,7β-dimethanesulfonyloxy-9α-fluoro-16α-methyl-1,4-pregnadiene-17α-ol-3,11,20-trione and 6β,7β-dimethanesulfonyloxy-9α-fluoro-16β-methyl-1,4-pregnadiene-17α-ol-3,11,20-trione.

C. 6-Azido-9α-fluoro-11-oxygenated-16-methyl-1,4,6-pregnatriene-17α-ol-3,20-diones 1. In a manner similar to that described in Example 1D, treat 1.2 g. of unpurified 6β,7β-dimethanesulfonyloxy-9α-fluoro-16α-methyl-1,4-pregnadiene-11β,17α-diol-3,20-dione prepared in Example 19B(1) with 4.91 g. of sodium azide in 15 ml. of dimethylformamide at room temperature for 24 hours. Isolate the resultant product in a manner similar to that described in Example 1D to obtain 0.97 g. of 6-azido-9α-fluoro-16α-methyl-1,4,6-pregnatriene-11β,17α-diol-3,20-dione. Purify by chromatographing on a silica gel column, eluting with ethyl acetate-chloroform (1:2). Combine like eluates as determined by thin layer chromatography to obtain 6-azido-9α-fluoro-16α-methyl-1,4,6-pregnatriene-11β,17α-diol-3,20-dione. Yield = 200 mg. (24% theory). Further purify by recrystallizing from methanol; m.p. 150°C (decomp) $[\alpha]_D^{26°}$ +41.8° (dimethylformamide) $\lambda_{max}^{methanol}$ 249 nm ($\epsilon$=16,400);313nm ($\epsilon$=9,100); $\nu_{nujol}$ 4.71μ ($N_3$); n.m.r. (dmso $d_6$/$D_2O$) δ 0.82 ($C_{16}$-$CH_3$; d J, 7Hz); 0.93 ($C_{13}$-$CH_3$); 1.47 ($C_{10}$-$CH_3$); 2.1 ($C_{20}$-$CH_3$); 4.26 (11α-H; mult); 5.65 ($C_7$-H; d J2Hz); 6.22($C_4$-H); 6.32 ($C_2$-H; d,d J10,2-Hz); 7.41 ($C_1$-H; d,J10Hz). 2. Similarly, treat each of the b 6β,7β-dimethanesulfonyloxy-1,4-pregnadienes prepared in Example 19B(2) with sodium azide in dimethylformamide to obtain the following compounds, respectively; 6-azido-9α-fluoro-16β-methyl-1,4,6-pregnatriene-11β,17α-diol-3,20-dione; 6-azido-9α-fluoro-16α-methyl-1,4,6-pregnatriene-17α-ol-3,11,20-trione and 6-azido-9α-fluoro-16β-methyl-1,4,6-pregnatriene-17α-ol-3,11,20-trione.

EXAMPLE 20

6-Azido-21-desoxy-4,6-pregnadiene-3,20-diones

A. 6β,7β-dihydroxy-21-desoxy-4-pregnene-3,20-diones

1. In a manner similar to that described in Example 1B, treat 2.9 g. of 17α-acetoxy-4,6-pregnadiene-3,20-dione with 2 g. of osmium tetroxide in 115 ml. of dioxane and 4 ml. of pyridine for 2.5 days at room temperature. Isolate the resultant product in a manner similar to that described and purify by chromatography on silica gel column, eluting with ethyl acetate-chloroform (1:1). Evaporate the combined eluates to a residue comprising 1.73 g. (55% theory) of a product mixture containing 6β,7β-dihydroxy-17α-acetoxy-4-pregnene-3,20-dione and 6α,7α-dihydroxy-17α-acetoxy-4-pregnene-3,20-dione (ratio of 6β,7β-diol to 6α,7α-diol about 4:1).

Separate the isomeric 6.7-dihydroxy-product mixture via preparative thin layer chromatography to obtain 6β,7β-dihydroxy-17α-acetoxy-4-pregnene-3,20-dione and 6α,7α-dihydroxy-17α-acetoxy-4-pregnene-3,20-dione.

Further purify 6β,7β-dihydroxy-17α-acetoxy-4-pregnene-3,20-dione by recrystallization from ethyl acetate $[\alpha]_D^{26°}$ +27.5°(dimethylformamide) $\lambda_{max}^{methanol}$ 240 nm ($\epsilon$=14,100) n.m.r. ($CDCl_3$) δ 0.71 ($C_{13}$-$CH_3$); 1.37 ($C_{10}$-$CH_3$); 3.42 (7α-H; d,d J7,3Hz); 4.21 (6α-H; d, J3.5 Hz); 5.88 ($C_4$-H).

Further purify the 6α,7α-dihydroxy-17α-acetoxy-4-pregnene-3,20-dione by recrystallization from ethyl acetate $[\alpha]_D^{26°}$ +56.9° (dimethylformamide) $\lambda_{max}^{methanol}$ 251 nm ($\epsilon$=15,300); n.m.r. ($CDCl_3$)δ0.67 ($C_{13}$-$CH_3$); 1.21 ($C_{10}$-$CH_3$); 4.00 (7β-H; d,J 3.5 Hz); 4.33 (6β-H; t,J 2.5 Hz); 6.25 ($C_4$-H: d J 2Hz).

2. In similar manner, treat each of the following 21-desoxy-4,6-pregnadiene-3,20-diones with osmium tetroxide in dioxanepyridine:

1. 16β-methyl-16α,17α-oxido-4,6-pregnadiene-3,20-dione,
2. 9α-fluoro-16α,17α-iso-propylidenedioxy-4,6-pregnadiene-11β-ol-3,20-dione,
3. 9α,21-difluoro-16α-methyl-4,6-pregnadiene-11β,17α-diol-3,20-dione,
4. 9α,21-difluoro-16β-methyl-4,6-pregnadiene-17α-ol-3,11,20-trione,
5. 9α,11β-dichloro-21-fluoro-17α-acetoxy-1,4,6-pregnatriene-3,20-dione,
6. 9α,11β-dichloro-1,4,6-pregnatriene-3,20-dione,
7. 9α,11β-dichloro-21-iodo-17α-acetoxy-1,4,6-pregnatriene-3,20-dione,
8. 16β-methyl-4,6-pregnadiene-3,11,20-trione,
9. 16α-methyl-4,6-pregnadiene-3,11,20-trione.

Isolate and purify each of the resultant products in a manner similar to that described in Example 1B to obtain respectively:

1. 6β,7β-dihydroxy-16β-methyl-16α,17α-oxido-4-pregnene-3,20-dione,
2. 6β,7β-dihydroxy-9α-fluoro-16α,17α-iso-propylidene-dioxy-4-pregnene-11β-ol-3,20-dione,
3. 6β,7β-dihydroxy-9α,21-difluoro-16α-methyl-4-pregnene-11β,17α-diol-3,20-dione,
4. 6β,7β-dihydroxy-9α,21-difluoro-16β-methyl-4-pregnene-17α-ol-3,11,20-trione,
5. 6β,7β-dihydroxy-9α,11β-dichloro-21-fluoro-17α-acetoxy1,4-pregnadiene-3,20-dione, 6. 6β,7β-dihydroxy-9α,11β-dichloro-1,4-pregnadiene-3,20-dione, 7. 6β, 7β-dihydroxy-9α,11β-dichloro-21-iodo-17α-acetoxy-1,4-pregnadiene-3,20-dione, 8. 6β,7β-dihydroxy-16β-methyl-4-pregnene-3,11,20-trione, 9. 6β7β-dihydroxy-16α-methyl-4-pregnene-3,11,20-trione.

B.
6β,7β-Dimethanesulfonyloxy-21-desoxy-4-pregnene-3,20-diones

1. In a manner similar to that described in Example 1C, treat 6β,7β-dihydroxy-17α-acetoxy-4-pregnene-3,20-dione with methanesulfonyl chloride in pyridine and isolate the resultant product in a manner similar to that described to obtain 6β,7β-dimethanesulfonyloxy-17α-acetoxy-4-pregnene-3,20-dione. 2. In similar manner, treat each of the 6β,7β-dihydroxy-4-pregnenes prepared in above Example 20A(2) with methanesulfonyl chloride in pyridine. Isolate each of the resultant respective products in a manner similar to that described to obtain respectively:

1. 6β,7β-dimethanesulfonyloxy-16β-methyl-16α,17α-oxido-4-pregnene-3,20-dione, 2. 6β,7β-dimethanesulfonyloxy-9α-fluoro-16α,17α-isopropylidenedioxy-4-pregnene-11β-ol-3,20-dione, 3. 6β,7β-dimethanesulfonyloxy-9α,21-difluoro-16α-methyl-4-pregnene-11β,17α-diol-3,20-dione, 4. 6β,7β-dimethanesulfonyloxy-9α,21-difluoro16β-methyl-4-pregnene-17α-ol-3,11,20-trione, 5. 6β,7β-dimethanesulfonyloxy-9α,11β-dichloro-21-fluoro-17α-acetoxy-1,4-pregnadiene-3,20-dione, 6. 6β,7β-dimethanesulfonyloxy-9α,11β-dichloro-1,4-pregnadiene-3,20-dione, 7. 6β,7β-dimethanesulfonyloxy-9α,11β-dichloro-21-iodo-17α-acetoxy-1,4-pregnadiene-3,20-dione, 8. 6β,7β-dimethanesulfonyloxy-16β-methyl-4-pregnene-3,11,20-trione, 9. 6β,7β-dimethanesulfonyloxy-16α-methyl-4-pregnene-3,11,20-trione.

C. 6-Azido-21-desoxy-4,6-pregnadiene-3,20-diones

1. In a manner similar to that described in Example 6C, treat 6β,7β-dimethanesulfonyloxy-17α-acetoxy-4-pregnene-3,20-dione with sodium azide in aqueous methanol in the presence of acetic acid. Isolate and purify the resultant product in a manner similar to that described to obtain 6-azido-17α-acetoxy-4,6-pregnadiene-3,20-dione.

2. Similarly, treat each of the 6β,7β-dimethanesulfonyloxy-4-pregnenes obtained as described in Example 20B(2) with an azide salt in a nonreactive solvent according to procedures similar to those described in Example 1D, 6C and in Example 12 to obtain respectively:

1. 6-azido-16β-methyl-16α,17α-oxido-4,6-pregnadiene-3,20-dione, 2. 6-azido-9α-fluoro-16α,17α-iso-propylidenedioxy-4,6-pregnadiene-11β-ol-3,20-dione, 3. 6-azido-9α,21-difluoro-16α-methyl-4,6-pregnadiene-11α,17α-diol-3,20-dione, 4. 6-azido-9α,21-difluoro-16β-methyl-4,6-pregnadiene-17α-ol-3,11,20-trione, 5. 6-azido-9α,11β-dichloro-21-fluoro-17α-acetoxy-1,4,6-pregnatriene-3,20-dione, 6. 6-azido-9α,11β-dichloro-1,4,6-pregnatriene-3,20-dione, 7. 6-azido-9α,11β-dichloro-21-iodo-17α-acetoxy-1,4,6-pregnatriene-3,20-dione, 8. 6-azido-16β-methyl-4,6-pregnadiene-3,11,20-trione, 9. 6-azido-16α-methyl-4,6-pregnadiene-3,11,20,trione.

EXAMPLE 21

6-Azido-17α-acetoxy-1,4,6-pregnatriene-3,20-dione

A.
6β,7β-Dihydroxy-17α-acetoxy-1,4-pregnadiene-3,20-dione

In a manner similar to that described in Example 1B, treat 0.23 g. of 17α-acetoxy-1,4,6-pregnatriene-3,20-dione with 0.5 g. of osmium tetroxide in 15 ml. of dioxane and 0.5 ml. of pyridine for three days at room temperature. Isolate the resultant product in a manner similar to that described in Example 1B and purify by chromatographing on a silica gel column, eluting with chloroform-ethyl acetate (1:1). Combine the like eluates as determined by thin layer chromatography and evaporate the combined eluates to a residue comprising 6β,7β-dihydroxy-17α-acetoxy-1,4-pregnadiene-3,20-dione. Yield = 97 mg. (42% theory) n.m.r. (CDCl$_3$) δ0.73 (C$_{13}$-CH$_3$); 1.43 (C$_{10}$-CH$_3$); 3.38 (7α-H; mult); 4.22 (6α-H; d,J 4Hz); 6.20 (C$_4$-H; d,J 2Hz); 6.21 (C$_2$-H; d,d J10,2Hz); 7.05 (C$_1$-H; d,J10 Hz).

B.
6β,7β-Dimethanesulfonyloxy-17α-acetoxy-1,4-pregnadiene3,20-dione

In a manner similar to that described in Example 1C, treat 6β,7β-dihydroxy-17α-acetoxy-1,4-pregnadiene-3,20-dione with methanesulfonyl chloride in pyridine. Isolate the resultant product in a manner similar to that described to obtain 6β,7β-dimethanesulfonyloxy-17α-acetoxy-1,4-pregnadiene-3,20-dione which is used without further purification in Example 21C.

C. 6Azido-17α-acetoxy-1,4,6-pregnatriene-3,20-dione

In a manner similar to that described in Example 1D, treat 6β,7β-dimethanesulfonyloxy-17α-acetoxy-1,4-pregnadiene-3,20-dione with sodium azide in dimethylformamide. Isolate and purify the resultant product in a manner similar to that described in Example 1D to obtain 6-azido-17α-acetoxy-1,4,6-pregnatriene-3,20-dione.

EXAMPLE 22

6-Azido-17-oxygenated-4,6-androstadienes

A. 6β,7β-dihydroxy-4-androstene-3,17-dione and the 6α,7α-Epimer Thereof

In a manner similar to that described in Example 1B, treat 1.13 g. of 4,6-androstadiene-3,17-dione with 1 g. of osmium tetroxide in 30 ml. of dioxane and 2 ml. of pyridine at room temperature for three days under an atmosphere of nitrogen. Isolate the resultant product in a manner similar to that described to obtain a product mixture comprising 6β,7β-dihydroxy-4-androstene-3,17-dione and the 6α,7α-dihydroxy-epimer thereof. Separate the isomeric 6,7-dihydroxy product by chromatographing on silica gel plates, developing with chloroform-ethyl acetate-methanol (4.5:4.5:1). Combine like fractions, elute with ethyl acetate and evaporate the eluate to obtain 0.41 g. (33% theory) of 6β,7β-dihydroxy-4-androstene-3,17-dione. Further purify by recrystallization from ethyl acetate; $[\alpha]_D^{26°}$ +134.8° (acetone); $\lambda_{max}^{methanol}$ 238 nm ($\epsilon$=13,000); n.m.r. (dmso-d$_6$/D$_2$O) δ 0.87 (C$_{13}$-CH$_3$); 1.32 (C$_{10}$-CH$_3$); 3.30 (7α-H; d,d J5.5, 3.5 Hz); 4.10 (6α-H; d J 3.5 Hz); 5.75 (C$_4$-H).

Evaporate the second set of combined like eluates to a residue comprising 0.16 g. (13% theory) of 6α,7α-dihydroxy-4-androstene-3,17-dione. Further purify by recrystallization from methanol; $\lambda_{max}^{methanol}$ 240 nm ($\epsilon$=14,200) n.m.r. (dmso-d$_6$/D$_2$O) δ 0.85 (C$_{13}$-CH$_3$); 1.20 (C$_{10}$-CH$_3$); 3.88 (7β-H; d,J 4Hz); 4.23 (6β-H; t J2.5Hz); 6.01 (C$_4$-H; d J, 2Hz).

B.
6β,7β-Dimethanesulfonyloxy-4-androstene-3,17-dione

In a manner similar to that described in Example 1C, treat 6β,7β-dihydroxy-4-androstene-3,17-dione with methanesulfonyl chloride in pyridine. Isolate the resultant product in a manner similar to that described to obtain 6β,7β-dimethanesulfonyloxy-4-androstene-3,17-dione which is used without further purification in the step immediately following.

C. 6-Azido-4,6-androstadiene-3,17-dione

Dissolve 70 mgms. 6β,7β-dimethanesulfonyloxy-4-androstene-3,17-dione prepared in above Example 22B in 2 ml. of dimethylformamide. Add 120 mg. of sodium azide, then stir at room temperature under an atmosphere of nitrogen in the absence of light for 24 hours. Pour into water, then isolate the resultant product in a manner similar to that described in Example 1D to obtain 38 mg. of 6-azido-4,6-androstadiene-3,17-dione. Purify by chromatographing on preparative thin layer plates, developing with chloroform-ethyl acetate (2:1), combine like fractions, elute with ethyl acetate and evaporate eluate to obtain 24 mg. (37% theory) of 6-azido-4,6-androstadiene-3,17-dione. Purify further by recrystallization from methanol, m.p. 140°-143°C.

Conversion of 6α,7α-dihydroxy-4-androstene-3,17-dione to the corresponding 6α,7α-dimethanesulfonate ester by treatment with methanesulfonyl chloride in pyridine in a manner similar to that described in Example 22B followed by treatment of the resulting 6α,7α-dimethanesulfonyloxy-4-androstene-3,17-dione with sodium azide in dimethylformamide in a manner similar to that described in above Example 22C does not yield an identifiable amount of 6-azido-4,6-androstadiene-3,17-dione. Similarly, treatment of 6α,7α-dimethanesulfonyloxy-4-androstene-3,17-dione with sodium azide in aqueous methanol in the presence of acetic acid in a manner similar to that described in Example 6, does not yield an identifiable quantity of 6-azido-4,6-androstadiene-3,17-dione.

D. In a manner similar to that described in above Examples 22A, B and C, treat each of 4,6-androstadiene-17β-ol-3-one-17-acetate and 17α-methyl-4,6-androstadiene-17β-ol-3-one with osmium tetroxide in dioxane-pyridine to obtain 6β,7β-dihydroxy-4-androstene-17β-ol-3-one-17-acetate and 6β,7β-dihydroxy-17α-methyl-4-androstene-17β-ol-3-one, respectively. Treat each of the foregoing 6β,7β-dihydroxy-4-androstenes with methanesulfonyl chloride in pyridine to obtain respectively: 6β, 7β-dimethanesulfonyloxy-4-androstene-17β-ol-3-one-17-acetate and 6β,7β-dimethanesulfonyl-17α-methyl-4-androstene-17β-ol-3-one. Then treat the foregoing 6β,7β-dimethanesulfonyloxy-4-androstenes with sodium azide in dimethylformamide according to the procedure of Example 1D or in aqueous methanol in the presence of acetic acid according to the procedure of Example 6 to obtain respectively: 6-azido-4,6-androstadiene-17β-ol-3-one-17-acetate and 6-azido-17α-methyl-4,6-androstadiene-17β-ol-3-one.

EXAMPLE 23

6-Azido-17-oxygenated-1,4,6-androstatriene-3-ones

A. 6β,7β-Dihydroxy-1,4-androstadiene-3,17-dione

To 0.83 g. of 1,4,6-androstatriene-3,17-dione in 15 ml. of dioxane and 0.83 ml. of pyridine add 0.75 g. of osmium tetroxide. Stir the reaction mixture under an atmosphere of nitrogen at room temperature in the absence of light for two days. Isolate the resultant product in a manner similar to that described in Example 1B. Purify by chromatographing on thin layer plates developing with ethyl acetate-chloroform-methanol (4.5:4.5:1). Combine like fractions, elute with ethyl acetate, and evaporate the eluate to a residue comprising 6β,7β-dihydroxy-1,4-androstadiene-3,17-dione. Yield=445 mg. (48% theory). Further purify by recrystallization from methanol; $[\alpha]_D^{26°}$ +66.7° (acetone); $\lambda_{max}^{methanol}$ 244 nm (γ=15,300); n.m.r. (dmso-d$_6$/D$_2$O) δ0.89 (C$_{13}$-CH$_3$); 1.37 (C$_{10}$-CH$_3$); 3.25(7α-H; d,d J10,3Hz); 4.24 (6α-H; d,J3.5Hz); 6.11 (C$_4$-H; d,J 2Hz); 6.11 (C$_2$-H; d,d J10,2Hz); 7.18 (C$_1$H; d,J 10Hz).

B.
6β,7β-Dimethanesulfonyloxy-1,4-androstadiene-3,17-dione

In the manner similar to that described in Example 1C, treat 6β,7β-dihydroxy-1,4-androstadiene-3,17-dione with methanesulfonyl chloride in pyridine. Isolate the resultant product in a manner similar to that described to obtain 6β,7β-dimethanesulfonyloxy-1,4-androstadiene-3,17-dione.

C. 6-Azido-1,4,6-androstatriene-3,17-dione

In a manner similar to that described in Example 1D, treat 6β,7β-dimethanesulfonyloxy-1,4-androstadiene-3,17-dione with sodium azide in dimethylformamide. Isolate and purify the resultant product in a manner similar to that described to obtain 6-azido-1,4,6-androstatriene-3,17-dione.

D. In a manner similar to that described in above Example 23A, B, and C, treat each of 1,4,6-androstatriene-17β-ol-3-one-17-acetate and 17α-methyl-1,4,6-androstatriene-17β-ol-3-one with osmium tetroxide in dioxane pyridine to obtain respectively: 6β,7β-dihydroxy-1,4-androstadiene-17β-ol-3-one-17-acetate and 6β,7β-dihydroxy-17α-methyl-1,4-androstadiene-17β-ol-3-one. Treat one of the foregoing 6β,7β-dihydroxy-1,4-androstadienes with methanesulfonyl chloride in pyridine to obtain respectively: 6β,7β-dimethanesulfonyloxy-1,4-androstadiene-17β-ol-3-one-17-acetate and 6β,7β-dimethanesulfonyloxy-17α-methyl-1,4-androstadiene-17β-ol-3-one. Treat each of the foregoing 6β,7β-dimethanesulfonate esters with sodium azide in dimethyl-formamide followed by isolation and purification of each of the resultant products in a manner similar to that described to obtain respectively: 6-azido-1,4,6-androstatriene-17β-ol-3-one-17-acetate and 6-azido-17α-methyl-1,4,6-androstatriene-17β-ol-3-one.

EXAMPLE 24

6-Azido-17α-ethinyl-4,6-androstadiene-17β-ol-3-one

A. 6β,7β-Dihydroxy-17α-ethinyl-4-androstene-17β-ol-3-one

Add 1 g. of 6β,7β-dihydroxy-4-androstene-3,17-dione to 20 ml. of dimethylformamide and stir at room temperature under an atmosphere of argon. Add 1 equivalent of sodium acetylide (0.15 g.) in 0.8 ml. xylene in one portion. After one minute, add a large volume of water (200 ml.) to the reaction mixture, then extract with two portions of ethyl acetate. Wash the combined ethyl acetate extracts with two portions of water, dry over anhydrous magnesium sulfate, and evaporate to a residue comprising 6β,7β-dihydroxy-17α-ethinyl-4-androstene-17β-ol-3-one.

B. 6β,7β-Dimethanesulfonyloxy-17α-ethinyl-4-androstene-17β-ol-3-one

In a manner similar to that described in Example 1C, treat 6β,7β-dihydroxy-17α-ethinyl-4-androstene-17β-ol-3-one with methanesulfonyl chloride in pyridine. Isolate the resultant product in a manner similar to that described to obtain 6β,7β-dimethanesulfonyloxy-17α-ethinyl-4-androstene-17β-ol-3-one.

C. 6-Azido-17α-ethinyl-4,6-androstadiene-17β-ol-3-one

In a manner similar to that described in Example 6, treat 6β,7β-dimethanesulfonyloxy-17α-ethinyl-4-androstene-17β-ol-3-one with sodium azide in aqueous methanol in the presence of acetic acid. Isolate and purify the resultant product in a manner similar to that described in Example 6 to obtain 6-azido-17α-ethinyl-4,6-androstadiene-17β-ol-3-one.

EXAMPLE 25

6-Azido-4,6-Cholestadiene-3,20-dione

A. 6β,7β-Dihydroxy-4-cholestene-3-one

In a manner similar to that described in Example 1B, treat 4,6-cholestadiene-3-one with osmium tetroxide in dioxane and pyridine under an atmosphere of nitrogen followed by treatment of the 6β,7β-osmate ester thereby formed with hydrogen sulfide. Isolate and purify the resultant product in a manner similar to that described to obtain 6β,7β-dihydroxy-4-cholestene-3-one.

B. 6β,7β-Dimethanesulfonyloxy-4-cholestene-3-one

In a manner similar to that described in Example 1C, treat 6β,7β-dihydroxy-4-cholestene-3-one with methanesulfonyl chloride and pyridine. Isolate the resultant product in a manner similar to that described to obtain 6β,7β-dimethanesulfonyloxy-4-cholestene-3-one.

C. 6-Azido-4,6-Cholestadiene-3-one

In a manner similar to that described in Example 6C, treat 6β,7β-dimethanesulfonyloxy-4-cholestene-3-one with sodium azide in aqueous methanol in the presence of acetic acid. Isolate and purify the resultant product in a manner similar to that described to obtain 6-azido-4,6-cholestadiene-3-one.

EXAMPLE 26

6-Azido-16-methylene-4,6-pregnadiene-17α-ol-3,20-diones

A. 6β,7β-Dimethanesulfonyloxy-9α-fluoro-16-methylene-1,4-pregnadiene-11β,17α,21-triol-3,20-dione 21-acetate To a solution of 0.8 g. of 6β,7β-dimethanesulfonyloxy-9α-fluoro-16β-metyl-16α,17α-oxido-1,4-pregnadiene-11β,21-diol-3,20-dione 21-acetate in 17 ml. of acetic acid at room temperature, add 1.7 ml. of a 10% solution of hydrobromic acid in acetic acid. Allow the reaction mixture to stand at room temperature for thirty minutes, then dilute with two liters of water. Extract with methylene chloride and wash the combined methylene chloride extract with water and evaporate to a residue comprising 6β,7β-dimethanesulfonyloxy-9α-fluoro-16-methylene-1,4-pregnadiene-11β,17α,21-triol-3,20-dione 21-acetate.

B. 6-Azido-9α-fluoro-16-methylene-1,4,6-pregnatriene-11β,17α,21-triol-3,20-dione 21-acetate In a manner similar to that described in Example 1D, treat 6β,7β-dimethanesulfonyloxy-9α-fluoro-16-methylene-1,4-pregnadiene-11β,17α,21-triol-3,20-dione 21-acetate with sodium azide in dimethylformamide. Isolate and purify the resultant product in a manner similar to that described to obtain 6-azido-9α-fluoro-16-methylene-1,4,6-pregnatriene-11β,17α,21-triol-3,20-dione 21-acetate.

EXAMPLE 27

6-Azido-16-methylene-17α-hydroxy-4,6-pregnadiene-3,20-dione

In a manner similar to that described in Example 26, treat 6β,7β-dimethanesulfonyloxy-16β-methyl-16α,17α-oxido-4-pregnene-3,20-dione with hydrogen bromide in acetic acid; treat the resulting 6β,7β-dimethanesulfonyloxy-16-methylene-17α-hydroxy-4-pregnene-3,20-dione with sodium azide in dimethylformamide to obtain 6-azido-16-methylene-17α-hydroxy-4,6-pregnadiene-3,20-dione.

EXAMPLE 28

6-Azido-9α-fluoro-16-methylene-1,4,6-pregnatriene-11β,17α,21-triol-3,20-dione 17,21-diacetate

A. 6β,7β-Dimethanesulfonyloxy-16-methylene-1,4-pregnadiene-11β,17α,21-triol-3,20-dione 17,21-diacetate To a solution comprising 550 mg. of 6β,7β-dimethanesulfonyloxy-9α-fluoro-16β-methyl-16α,17α-oxido-1,4-pregnadiene-11β,21-diol-3,20-dione 21-acetate in 8 ml. of acetic acid and 80 mg. of p-toluenesulfonic acid. Cool to 5°C, add 4 mg. of trifluoroacetic anhydride. Allow the reaction mixture to stand at room temperature for 25 minutes, then pour into water and collect by filtration 6β,7β-dimethanesulfonyloxy-9α-fluoro-16-methylene-1,4-pregnadiene-11β,17α,21-triol-3,20-dione 17,21-diacetate.

B.
6-Azido-9α-fluoro-16-methylene-1,4,6-pregnatriene-11β,17α,21-triol-3,20-dione 17,21-diacetate In a manner similar to that described in Example 1D, treat 6β,7β-dimethanesulfonyloxy-9α-fluoro-16-methylene-1,4-pregnadiene-11β,17α,21-triol-3,20-dione 17,21-diacetate with sodium azide in dimethylformamide. Isolate and purify the resultant product in a manner similar to that described to obtain 6-azido-9α-fluoro-16-methylene-1,4,6-pregnatriene-11β,17α,21-triol-3,20-dione 17,21-diacetate.

Alternatively, by utilizing alkanoic acid other then acetic acid, e.g. propionic acid and valeric acid, in above procedure 28A, there is obtained the corresponding 17-lower alkanoate of this example. Thus, treatment of 6β,7β-dimethanesulfonyloxy-9α-fluoro-16β-methyl-16α,17α-oxido-1,4-pregnadiene-11β,21-diol-3,20 -dione 21-acetate with propionic acid and p-toluenesulfonic acid or with valeric acid and p-toluenesulfonic acid according to the procedure of Example 28A will yield respectively 6β,7β-dimethanesulfonyloxy-16-methylene-1,4-pregnadiene-11β,17α,21-triol-3,20-dione 17-propionate 21-acetate or 6β,7β-dimethanesulfonyloxy-16-methylene-1,4-pregnadiene-11β,17α,21-triol-3,20-dione 17-valerate 21-acetate. Treatment of each of the foregoing 6β,7β-dimethanesulfonyloxy-intermediates with sodium azide in dimethylformamide in the manner described in Example 28B will yield respectively 6-azido-9α-fluoro-16-methylene-1,4-pregnadiene-11β,17α,21-triol-3,20-dione 17-propionate 21-acetate or 6-azido-9α-fluoro-16-methylene-1,4-pregnadiene-11β,17α,21-triol-3,20-dione 17-valerate, 21-acetate.

EXAMPLE 29

Preparation of 6-Azido-6-dehydro-dexamethasone Utilizing Barium Azide

In a manner similar to that described in Example 1D, treat 6β,7β-dimethanesulfonyloxy-9α-fluoro-16α-methyl-1,4-pregnadiene-11β,17α,21-triol-3,20-dione 21-acetate (1 g.) with barium azide (4 g.) in dimethylformamide (16 ml.). Stir at room temperature in the absence of light under an atmosphere of argon for 24 hours. Isolate and purify the resultant product in a manner similar to that described in Example 1D to obtain 6-azido-9α-fluoro-16α-methyl-1,4,6-pregnatriene-11β,17α,21-triol-3,20-dione 21-acetate.

EXAMPLE 30

6-Azido-4,6-pregnadiene-11β,17α,21-triol-3,20-dione 21-acetate (6-Azido-6-dehydro-hydrocortisone 21-acetate)

In a manner similar to that described in Example 6A, treat 4,6-pregnadiene-11β,17α,21-triol-3,20-dione 21-acetate with osmium tetroxide in dioxane followed by treatment of the thereby formed 6β,7β-osmate ester with hydrogen sulfide to obtain 6β,7β-dihydroxy-4-pregnene-11β,17α-21-triol-3,20-dione 21-acetate. Treat the foregoing 6β,7β-dihydroxy-4-pregnene-with methanesulfonyl chloride in pyridine in the manner of Example 6B to obtain 6β,7β-dimethanesulfonyloxy-4-pregnene-11,β,17α,21-triol-3,20-dione 21-acetate.

Dissolve 0.9 g. of 6β,7β-dimethanesulfonyloxy-4-pregnene-11β,17α,21-triol-3,20-dione 21-acetate in a solution comprising 135 ml. of methanol, 2.25 ml. of water and 0.5 g. of orthoboric acid. Add 5.4 g. of sodium azide and stir the reaction mixture at room temperature in the absence of light for 24 hours. Isolate the resultant product in a manner similar to that described in Example 6C to obtain 6-azido-4,6-pregnadiene-11β,17α,21-triol-3,20-dione 21-acetate.

EXAMPLE 31

Preparation of 6-Azido-4,6-androstadiene-3,17-dione Via the 6β,7α-dimethanesulfonate ester A. 6β,7α-Dihydroxy-4-androstene-3,17-dione To 1 g. of 6α,7α-oxido-4-androstene-3,17-dione in 50 ml. of tetrahydrofuran, add 6 ml. of 25% aqueous perchloric acid and stir the reaction mixture for three hours at room temperature. Add chloroform to the reaction mixture and extract the organic solution with saturated aqueous sodium bicarbonate, then with water. Dry the organic solution over anhydrous magnesium sulfate and evaporate in vacuo to a residue comprising 6β,7α-dihydroxy-4-androstene-3,17-dione. Purify by crystallization from ethyl acetate. Yield = 520 mg.; $[\alpha]_D^{26°}$ + 94.2° acetone; $\lambda_{max}^{methanol}$ 238 nm ($\epsilon$ = 12,000) n.m.r. (dmso-$d_6$/$D_2O$) δ 0.87 ($C_{13}$-$CH_3$); 1.47 ($C_{10}$-$CH_3$); 3.74 (7β-H; mult); 4.00 (6α-H;d,J3Hz); 5.72 ($C_4$-H).

B.
6β,7α-Dimethanesulfonyloxy-4-androstene-3,17-dione

In a manner similar to that described in Example 1C, treat 6β,7α-dihydroxy-4-androstene-3,17-dione (150 mg.) in pyridine (5 ml.) with methanesulfonyl chloride (1 ml.) for two hours at room temperature. Isolate the resultant product in a manner similar to that described in Example 1C to obtain 180 mg. of 6β,7α-dimethanesulfonyloxy-4-androstene-3,17-dione which is used without further purification in the following step 31C.

C. 6-Azido-4,6-androstadiene-3,17-dione

In a manner similar to that described in Example 1D, treat 75 mg. of 6β,7α-dimethanesulfonyloxy-4-androstene-3,17-dione in 2.5 ml. of dimethylformamide with 150 mg. of sodium azide at room temperature for 24 hours. Isolate the resultant product in a manner similar to that described in Example 1D to obtain a mixture of at least three compounds containing 6-azido-4,6-androstadiene-3,17-dione. Further purify by thin layer chromatography on silica gel developing with ethyl acetate-chloroform (1:2). Combine like fractions and elute with ethyl acetate and evaporate the eluates in vacuo to a residue (yield =36 mg.) comprising a mixture of two compounds of which 9 mg. (17% theory) is 6-azido-4,6-androstadiene-3,17-dione. To isolate, further purify by successive thin layer chromatographic purifications on silica gel in a manner similar to that described to obtain 6-azido-4,6-androstadiene-3,17-dione.

EXAMPLE 32

6-Azido-4,6-pregnadiene-17α,21-diol-3,11,20-trione 21-acetate

A. To 250 mg. of 6α,7α-oxido-4-pregnene-17α,21-diol-3,11,20-trione 21-acetate in 20 ml. of acetone, add 1.5 ml. of 25% aqueous perchloric acid. Stir the reaction mixture at room temperature for 7 hours, filter, and add ethyl acetate to the filtrate. Wash the resultant organic solution with saturated aqueous sodium bicarbonate solution and then with water, dry the organic solution over anhydrous magnesium sulfate and evaporate to a residue comprising 6β,7α-dihydroxy-4-pregnene-17α,21-diol-3,11,20-trione 21-acetate. Purify by recrystallizing from methanol; $\lambda_{max}^{methanol}$ 231 nm (ε=13,000) n.m.r. (dmso-d$_6$/D$_2$O)δ 0.52 (C$_{13}$-CH$_3$); 1.58 (C$_{10}$-CH$_3$); 3.50 (7β-H; mult); 4.11 (6α-H; d,J3.5Hz); 5.87 (C$_4$-H).

B. In a manner similar to that described in Example 31B, treat 0.1 g. of 6β,7α-dihydroxy-4-pregnene-17α,21-diol-3,11,20-trione 21-acetate with 1 ml. of methanesulfonyl chloride in 5 ml. of pyridine at room temperature for two hours. Isolate the resultant product in a manner described to obtain 120 mg. of 6β,7α-dimethanesulfonyloxy-4-pregnene-17α,21-diol-3,11,20-trione 21-acetate. Treat this 6β,7α-dimethanesulfonyloxy-4-pregnene with 200 mg. of sodium azide in 4 ml. of dimethylformamide at room temperature for 24 hours. Isolate and purify the resultant product in a manner similar to that described in Example 31C to obtain a product mixture containing 6-azido-4,6-pregnadiene-17α,21-diol-3,11,20-trione 21-acetate in about 20% theoretical yield as determined by n.m.r. spectroscopy. Chromatograph further on silica gel to obtain 6-azido-4,6-pregnadiene-17α,21-diol-3,11,20-trione 21-acetate.

We claim:

1. The process for the manufacture of a 3-keto-6-azido-4,6-bis-dehydro-steroid of the pregnane and androstane series which comprises treating a 3-keto-6β,7-dihydrocarbonsulfonyloxy-4-dehydro-steriod of the pregnane and androstane series, said hydrocarbonsulfonyloxy having up to 12 carbon atoms, with an azide reagent selected from the group consisting of an alkali metal azide, an alkaline earth metal azide, a tetralower alkylammonium azide and a tetra-lower alkylguanidinium azide, in a non-reactive organic solvent.

2. The process of claim 1 wherein said 3-keto-6β,7-dihydrocarbonsulfonyloxy-4-dehydro-steroid is a 3-keto-6β,7β-dimethanesulfonyloxy-4-dehydro-steroid of the pregnane and androstane series.

3. The process of claim 1 wherein said azide reagent is an alkali metal azide, and said 3-keto-6β,7-dihydrocarbonsulfonyloxy-4-dehydro-steroid is a 3-keto-6β,7β-dimethanesulfonyloxy-4-dehydro-steroid of the pregnane series.

4. The process of claim 1 wherein said 3-keto-6β,7-dihydrocarbonsulfonyloxy-4-dehydro-steroid is a 3,20-diketo-6β,7β-dimethanesulfonyloxy-1,4-pregnadiene-17α,21-diol 21-lower alkanoate, said azide reagent is sodium azide, and said non-reactive organic solvent is dimethylformamide, whereby is formed a 3,20-diketo-6-azido-1,4,6-pregnatriene-17α,21-diol-21-lower alkanoate.

5. The process according to claim 1 wherein said 3-keto-6β,7-dihydrocarbonsulfonyloxy-4-dehydro-steriod is a 3,20-diketo-6β,7β-dimethanesulfonyloxy-1,4-pregnadiene-17α,21-diol 21-lower alkanoate having a halogen at C-9 and a β-hydroxyl or keto function at C-11, said azide reagent is sodium azide, and said nonreactive organic solvent is dimethylformamide.

6. The process of claim 1 wherein said 3-keto-6β,7-dihydrocarbonsulfonyloxy-4-dehydro-steroid is a 3-keto-6β,7β-dimethanesulfonyloxy-4-dehydro-steroid of the pregnane and androstane series, said azide reagent is tetra-n-butyl-ammonium azide and said non-reactive organic solvent is chloroform.

7. The process according to claim 5 wherein said 3-keto-6β,7-dihydrocarbonsulfonyloxy-4-dehydro-steroid is 6β,7β-dimethanesulfonyloxy-9α-fluoro-16α-methyl-1,4-pregnadiene-11β,17α,21-triol-3,20-dione 21-acetate whereby is formed 6-azido-9α-fluoro-16α-methyl-1,4,6-pregnatriene-11β,17α,21-triol-3,20-dione 21-acetate.

8. The process according to claim 5 wherein said 3-keto-6β,7-dihydrocarbonsulfonyloxy-4-dehydro-steroid is 6β,7β-dimethanesulfonyloxy-9α-fluoro-16β-methyl-1,4-pregnadiene-11β,17α,21-triol-3,20-dione 21-acetate whereby is formed 6-azido-9α-fluoro-16β-methyl-1,4,6-pregnatriene-11β,17α,21-triol-3,20-dione 21-acetate.

9. The process according to claim 5 wherein said 3-keto-6β,7-dihydrocarbonsulfonyloxy-4-dehydro-steroid is 6β,7β-dimethanesulfonyloxy-9α-fluoro-16α,17α-iso-propylidenedioxy-1,4-pregnadiene-11β,21-diol-3,20-dione 21-acetate whereby is formed 6-azido-9α-fluoro-16α,17α-iso-propylidenedioxy-1,4,6-pregnatriene-11β,21-diol-3,20-dione 21-acetate.

10. The process according to claim 5 wherein said 3-keto-6β,7-dihydrocarbonsulfonyloxy-4-dehydro-steroid is 6β,7β-dimethanesulfonyloxy-9α-fluoro-1,4-pregnadiene-11β,16α,17α,21-tetrol-3,20-dione 16,21-diacetate whereby is formed 6-azido-9α-fluoro-1,4,6-pregnatriene-11β,16α,17α,21-tetrol-3,20-dione 16,21-diacetate.

11. The process according to claim 1 wherein said 3-keto-6β,7-dihydrocarbonsulfonyloxy-4-dehydro-steroid is a 3,20-diketo-6β,7β-dimethanesulfonyloxy-1,2-dihydro-4-pregene-17α,21-diol 21-lower alkanoate having a halogen at C-9 and a β-hydroxyl or a keto function at C-11, wherein said azide reagent is sodium azide, and said non-reactive organic solvent is an aqueous lower alkanol in the presence of a weak acid.

12. The process according to claim 11 wherein said 3-keto-6β,7-dihydrocarbonsulfonyloxy-4-dehydro steroid is 6β,7β-dimethanesulfonyloxy-9α-fluoro-16α-methyl-4-pregnene-11β,17α, 21-triol-3,20-dione 21-acetate and said non-reactive organic solvent is aqueous methanol in the presence of acetic acid whereby is formed 6-azido-9α-fluoro-16α-methyl-4,6-pregnadiene-11β,17α,21-triol-3,20-dione 21-acetate.

13. The process according to claim 11 wherein said 3-keto-6β,7-dihydrocarbonsulfonyloxy-4-dehydro-steroid is 6β,7β-dimethanesulfonyloxy-9α-fluoro-16β-methyl-4-pregnene-11β,17α,21-triol-3,20-dione 21-acetate and said non-reactive organic solvent is aqueous methanol in the presence of acetic acid whereby is formed 6-azido-9α-fluoro-16β-methyl-4,6-pregnadiene-11β,18α,21-triol-3,20-dione 21-acetate.

14. The process according to claim 2 wherein said 3-keto-6β,7β-dihydrocarbonsulfonyloxy-4-dehydro-steroid is prepared by treating a 3-keto-4,6-bis-dehydro-steroid of the pregnane and androstane series unsubstituted at C-6 and C-7 with osmium tetroxide in a solvent selected from the group consisting of a saturated halogenated hydrocarbon and a saturated ether, followed by reductive cleavage of the thereby formed 6β,7β-osmate ester and treating the resulting 3-keto-6β,7β-dihydroxy-4-dehydro-steroid of the pregnane and androstane series with a hydrocarbonsulfonyl halide in a tertiary amine.

15. The process of claim 14 wherein said hydrocarbonsulfonyl halide in a tertiary amine is methanesulfonyl chloride in pyridine.

16. A compound selected from the group consisting of a 3-keto-6β,7β-dihydroxy-4-dehydro-steroid derivative of the following formulae I and II and the 1-dehydro analogs thereof:

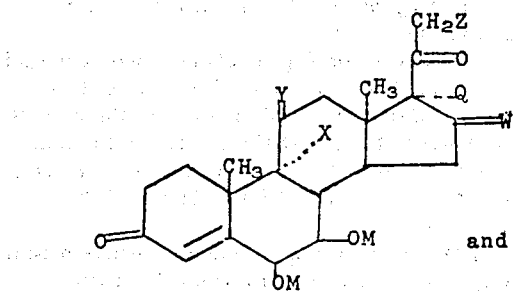

I

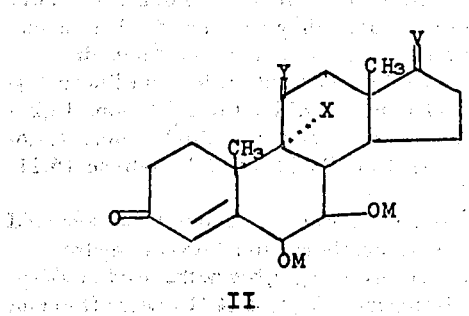

II wherein M is an acyl radical of a hydrocarbonsulfonic acid having up to 12 carbon atoms,
Q is a member selected from the group consisting of hydrogen, hydroxy and OR, R being an acyl radical of a hydrocarbon carboxylic acid having up to 12 carbon atoms;
V is a member selected from the group consisting of oxygen, (H, β-OR$_1$), (α-methyl, β-OR$_1$), (α-lower alkinyl, βOR$_1$) and (α-halogenoalkinyl β-OR$_1$) wherein R$_1$ is a member selected from the group consisting of hydrogen and lower alkanoyl;
W is a member selected from the group consisting of $$\begin{matrix} & H \\ C & \\ & H, \end{matrix}$$

(H, α-lower alkyl), (H, β-lower alkyl), (H, α-OH), (H, α-OR′) wherein R′ is an acyl radical of a hydrocarbon carboxylic acid having up to 12 carbon atoms, =CHT when Q is other than hydrogen wherein T is a member selected from the group consisting of hydrogen, lower alkyl, fluorine, chlorine, and W and Q together is alkylidenedioxy;
X is a member selected from the group consisting of hydrogen and halogen having an atomic weight less than 100;
Y is a member selected from the group consisting of $$\begin{matrix} & H \\ C & \\ & H \end{matrix}$$

provided X is hydrogen, oxygen, (H,βOH), and (H, β-halogen of atomic weight less than 100) provided X is halogen;
Z is a member selected from the group consisting of OR″ (R″ being an acyl radical of a hydrocarbon carboxylic acid having up to 12 carbon atoms), hydrogen and halogen, and Z together with Q is a member selected from the group consisting of alkylidenedioxy and alkylorthoalkanoate.

17. A compound according to claim 16 wherein M is methanesulfonyl.

18. A compound according to claim 16, formula I, wherein M is methanesulfonyl, Q is hydroxy or lower alkanoyloxy and Z is lower alkanoyloxy, or Z together with Q is alkylidenedioxy.

19. A compound according to claim 16, formula I, wherein M is methanesulfonyl, X is fluorine, Y is (H, βOH) or oxygen, Q is hydroxy or lower alkanoyloxy, and Z is lower alkanoyloxy or Z together with Q is alkylidenedioxy.

20. A compound according to claim 19 wherein W is (H,methyl).

21. A 1-dehydro compound according to claim 20 wherein Q and Z are propionyloxy, said compound being 6β,7β-dimethanesulfonyloxy-9α-fluoro-16-methyl-1,4-pregnadiene-11β,17α,21-triol-3,20-dione 17,21-dipropionate.

22. A compound according to claim 19 wherein Y is (H,βOH) and W is a member selected from the group consisting of (H,αlower alkyl), (H,β-lower alkyl), (H, α-OH), (H, α-OR′), or W and Q together are alkylidenedioxy.

23. A compound according to claim 22 wherein W is (H,α-methyl and Z is acetoxy, said compound being 6β,7β-dimethanesulfonyloxy-9α-fluoro-16α-methyl-4-pregnene-11β,17α,21-triol-3,20-dione 21-acetate.

24. A compound according to claim 22 wherein W is (H,β-methyl) and Z is acetoxy, said compound being 6β,7β-dimethanesulfonyloxy-9α-fluoro-16β-methyl-4-pregnene-11β,17α,21-triol-3,20-dione 21-acetate.

25. A 1-dehydro compound according to claim 22 wherein W is (H,α-methyl) and Z is acetoxy, said compound being 6β,7β-dimethanesulfonyloxy-9α-fluoro-16α-methyl-1,4-pregnadiene-11β,17α,21-triol-3,20-dione 21-acetate.

26. A 1-dehydro compound according to claim 22 wherein W is (H,β-methyl) and Z is acetoxy, said compound being 6β,7β-dimethanesulfonyloxy-9α-fluoro-16β-methyl-1,4-pregnadiene-11β, 17α,21-triol-3,20-dione 21-acetate.

27. A compound according to claim 22 wherein W is α-lower alkanoyloxy.

28. A 1-dehydro compound according to claim 27 wherein W and Z are acetoxy, said compound being 6β, 7β-dimethanesulfonyloxy-9α-fluoro-1,4-pregnadiene-11β,16α, 17α,21-tetrol-3,20-dione 16,21-diacetate.

29. A compound according to claim 22 wherein Z is acetoxy and W and Q together are iso-propylidenedioxy, said compound being a member selected from the group consisting of 6β,7β-dimethanesulfonyloxy-9α-fluoro-16α,17α-iso-propylidenedioxy-4-pregnene-11β,21-diol-3,20-dione 21-acetete and the 1-dehydro analog thereof.

30. A 1-dehydro compound according to claim 16, formula I, wherein M is methanesulfonyl, Q is hydroxy, W is (H, α-methyl), X is fluorine, Y is (H, (H,βOH) and Z is hydrogen, said compound being 6β,7β-dimethanesulfonyloxy-9α-fluoro-11β,17α-dihydroxy-16α-methyl-1,4-pregnadiene-3,20-dione.

31. 6β,7β-dihydroxy-9α-fluoro-16β-methyl-16α,17α-oxido-1,4-pregnadiene-11β,21-diol-3,20-dione 21-acetate.

32. 6β,7β-dihydroxy-9α-fluoro-16β-methyl-16α,17α-oxido-1,4-pregnadiene-11β-ol-3,20-dione.

* * * * *

UNITED STATES PATENT OFFICE
CERTIFICATE OF CORRECTION

Patent No. 3,931,167  Dated January 6, 1976

Inventor(s) Michael J. Green et al

It is certified that error appears in the above-identified patent and that said Letters Patent are hereby corrected as shown below:

Column 2, line 8, "perdominating" should read ---predominating---; line 22, "bis-dihydro" should read ---bis-dehydro---. Column 11, line 57, "introductions of" should read ---introduction of---. Column 12, line 21, "1,4-pregnatriene" should read ---1,4,6-pregnatriene---. Column 21, line 33, " $\mathscr{L}$ methanol$_{max}$" should read --- $\lambda$ methanol$_{max}$". Column 23, line 7, "--16β,17β--" should read ---16α,17α---; line 13, "--11α,21--" should read ---11β,21---; line 19, "--11α,21--" should read ---11β,21---. Column 32, line 53, "--21,01--" should read ---21-ol---. Column 33, line 17, "--11α,21--" should read ---11β,21---; line 46, "11. 60β,7β--" should read ---11. 6β,7β---; line 59, "---           ---" should read ---16. 6β,7β-dimethanesulfonyloxy-9α,11β-dichloro-1,4-pregnadiene-17α,21-diol-3,20-dione 21-acetate---. Column 34, line 6, "--18β(2)--" should read ---18B(2)---; line 41, "--9α,11α--" should read ---9α,11β---; line 59, "--11β,17α-dioe--" should read ---11β,17α-diol---. Column 37, line 62, "--11α,17α--" should read ---11β,17α---. Column 42, line 12, "--16β-metyl--" should read ---16β-methyl---; line 63, "--4 mg.--" should read ---4 ml.---. Column 46, line 53, Claim 13, "--11β,18α,21--" should read ---11β,17α,21---.

Signed and Sealed this

Twenty-sixth Day of October 1976

[SEAL]

Attest:

RUTH C. MASON  
Attesting Officer

C. MARSHALL DANN  
Commissioner of Patents and Trademarks